United States Patent
Honda et al.

(10) Patent No.: US 11,781,140 B2
(45) Date of Patent: *Oct. 10, 2023

(54) ANTISENSE NUCLEIC ACID INDUCING SKIPPING OF EXON 51

(71) Applicants: NIPPON SHINYAKU CO., LTD., Kyoto (JP); NATIONAL CENTER OF NEUROLOGY AND PSYCHIATRY, Kodaira (JP)

(72) Inventors: Yu Honda, Ibaraki (JP); Kaname Muchima, Ibaraki (JP); Takahiro Fukui, Ibaraki (JP); Saki Hasegawa, Ibaraki (JP); Shin'ichi Takeda, Tokyo (JP); Yoshitsugu Aoki, Tokyo (JP)

(73) Assignees: NIPPON SHINYAKU CO., LTD., Kyoto (JP); NATIONAL CENTER OF NEUROLOGY AND PSYCHIATRY, Kodaira (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/895,186

(22) Filed: Aug. 25, 2022

(65) Prior Publication Data

US 2023/0097387 A1 Mar. 30, 2023

Related U.S. Application Data

(63) Continuation of application No. PCT/JP2021/007286, filed on Feb. 26, 2021.

(30) Foreign Application Priority Data

Feb. 28, 2020 (JP) ................. 2020-033483

(51) Int. Cl.
C07H 21/04 (2006.01)
C12N 15/113 (2010.01)
A61P 21/00 (2006.01)

(52) U.S. Cl.
CPC ............ *C12N 15/113* (2013.01); *A61P 21/00* (2018.01); *C12N 2310/11* (2013.01); *C12N 2310/314* (2013.01); *C12N 2310/3233* (2013.01); *C12N 2310/51* (2013.01); *C12N 2320/33* (2013.01)

(58) Field of Classification Search
None
See application file for complete search history.

(56) References Cited

U.S. PATENT DOCUMENTS

2007/0082861 A1   4/2007  Matsuo et al.
2010/0130591 A1   5/2010  Sazani et al.
2015/0045413 A1   2/2015  De Visser et al.
2017/0067048 A1   3/2017  Wakayama et al.
2019/0330626 A1  10/2019  Rigo et al.

FOREIGN PATENT DOCUMENTS

| JP | 2012-506703 A | 3/2012 |
| JP | 2015-509922 A | 4/2015 |
| WO | WO-2002/024906 A1 | 3/2002 |
| WO | WO-2004/048570 A1 | 6/2004 |
| WO | WO-2004/083432 A1 | 9/2004 |
| WO | WO-2006/000057 A1 | 1/2006 |
| WO | WO-2009/054725 A2 | 4/2009 |
| WO | WO-2010/048586 A1 | 4/2010 |
| WO | WO-2010/050801 A1 | 5/2010 |
| WO | WO-2010/050802 A2 | 5/2010 |
| WO | WO-2015/137409 A1 | 9/2015 |
| WO | WO-2019/241385 A2 | 12/2019 |

OTHER PUBLICATIONS

Aartsma-Rus, Annemieke et al., "Targeted exon skipping as a potential gene correction therapy for Duchenne muscular dystrophy," Neuromuscular Disorders 12:S71-S77 (2002).
Aoki Y. et al., "In-frame Dystrophin Following Exon 51-Skipping Improves Muscle Pathology and Function in the Exon 52-Deficient mdx Mouse," Molecular Therapy 18:1995-2005 (2010).
Echigoya, Y. et al., "Quantitative Antisense Screening and Optimization for Exon 51 Skipping in Duchenne Muscular Dystrophy," Molecular Therapy vol. 25, No. 11, 2561-2572 (2017).
International Search Report and Written Opinion of the ISA dated Apr. 27, 2021 for PCT/JP2021/007286.
Matsuo, M., "Duchenne/Becker muscular dystrophy: from molecular diagnosis to gene therapy," Brain and Development 18:167-172 (1996).
Monaco A. P. et al., "An Explanation for the Phenotypic Differences between Patients Bearing Partial Deletions of the DMD Locus," Genomics 2:90-95 (1988).
Nakano, S. et al., "Exon-skipping events in candidates for clinical trials of morpholino," Pediatrics International 53:524-529 (2011).
Shimizu-Motohashi, Y. et al., "Restoring Dystrophin Expression in Duchenne Muscular Dystrophy: Current Status of Therapeutic Approaches," J. Pers. Med., 2019, vol. 9, pp. 1-14.
Wilton, S. D. et al., "Antisense Oligonucleotide-induced Exon Skipping Across the Human Dystrophin Gene Transcript," Molecular Therapy 15:1288-1296 (2007).

*Primary Examiner* — Kimberly Chong
(74) *Attorney, Agent, or Firm* — BANNER & WITCOFF, LTD

(57) ABSTRACT

The present specification provides a drug that causes highly-efficient skipping of exon 51 in the human dystrophin gene. The present specification provides an antisense oligomer having an activity to induce skipping of exon 51 in the human dystrophin gene.

19 Claims, 10 Drawing Sheets
Specification includes a Sequence Listing.

ANTISENSE NUCLEIC ACID INDUCING SKIPPING OF EXON 51

REFERENCE TO RELATED APPLICATIONS

This application is a Continuation Application of International Application No. PCT/JP2021/007286, filed Feb. 26, 2021, and claims benefit of Japanese Patent Application No. 2020-033483, filed Feb. 28, 2020, the entire contents of which are incorporated by reference herein.

SEQUENCE LISTING

The instant application contains a Sequence Listing XML which has been submitted electronically and is hereby incorporated by reference in its entirety. Said Sequence Listing XML copy, created on Jul. 26, 2022, is named G2505-sequence-listing-ST26.xml and is 163,585 bytes in size.

TECHNICAL FIELD

The present invention relates to an antisense oligomer which induces skipping of exon 51 in the human dystrophin gene, and a pharmaceutical composition comprising the antisense oligomer.

BACKGROUND ART

Duchenne muscular dystrophy (DMD) is the most frequent and severe form of hereditary progressive muscular atrophy that is developed in one in about 3,500 newborn boys. Although the motor functions in DMD patients are rarely different from healthy humans in infancy and childhood, their muscle weakness is observed in children from around 4 to 5 years old. Then, muscle weakness in DMD patients progresses to the loss of ambulation by about 12 years old and death due to cardiac or respiratory insufficiency in the twenties. At present, there is no sufficient therapy for DMD, and it has been strongly desired to develop an effective therapeutic agent.

DMD is known to be caused by a mutation in the dystrophin gene. The dystrophin gene is located on X chromosome and is a huge gene consisting of 2.2 million DNA base pairs. DNA is transcribed into mRNA precursors, and introns are removed by splicing to synthesize mRNA of 11,058 bases corresponding to a translated region, in which 79 exons are joined together. This mRNA is translated into 3,685 amino acids to produce the dystrophin protein. The dystrophin protein is associated with the maintenance of membrane stability in muscle cells and necessary to make muscle cells less fragile. The dystrophin gene from patients with DMD contains a mutation and hence, the dystrophin protein, which is functional in muscle cells, is rarely expressed. Therefore, the structure of muscle cells cannot be maintained in the body of the patients with DMD, leading to a large influx of calcium ions into muscle cells. Consequently, an inflammation-like response occurs to promote fibrosis to make the regeneration of muscle cells difficult.

Becker muscular dystrophy (BMD) is also caused by a mutation in the dystrophin gene. The symptoms involve muscle weakness accompanied by atrophy of muscle but are typically mild and slow in the progress of muscle weakness, when compared to DMD. In many cases, its onset is in adulthood. Differences in clinical symptoms between DMD and BMD are considered to reside in whether the reading frame for amino acids on the translation of dystrophin mRNA into the dystrophin protein is disrupted by the mutation or not (Non Patent Literature 1). More specifically, in DMD, the presence of mutation shifts the amino acid reading frame and thereby the functional dystrophin protein is rarely expressed, whereas in BMD the dystrophin protein that functions, though imperfectly, is produced because the amino acid reading frame is preserved, while a part of the exons are deleted by the mutation.

Exon skipping is expected to serve as a method for treating DMD. This method involves modifying splicing to restore the amino acid reading frame of dystrophin mRNA and induce expression of the dystrophin protein having the function partially restored (Non Patent Literature 2). The amino acid sequence part, which is a target of exon skipping, will be lost. For this reason, the dystrophin protein expressed by this treatment becomes shorter than normal one but since the amino acid reading frame is maintained, the function to stabilize muscle cells is partially retained. Consequently, it is expected that exon skipping will lead DMD to the similar symptoms to that of BMD which is milder. The exon skipping approach has passed the animal tests using mice or dogs and now is currently assessed in clinical trials on human DMD patients.

The skipping of an exon can be induced by binding of antisense nucleic acids targeting either 5' or 3' splice site or both sites, or exon-internal sites. An exon will be included in the mRNA only when both splice sites thereof are recognized by the spliceosome complex. Thus, exon skipping can be induced by targeting the splice sites with antisense nucleic acids. Furthermore, the binding of an SR protein to an exonic splicing enhancer (ESE) is considered necessary for an exon to be recognized by the splicing mechanism. Accordingly, exon skipping can also be induced by targeting ESE.

Since a mutation of the dystrophin gene may vary depending on DMD patients, antisense nucleic acids need to be designed based on the site or type of respective genetic mutation. In the past, antisense nucleic acids that induce exon skipping for all 79 exons were produced by Steve Wilton, et al., University of Western Australia (Non Patent Literature 3), and the antisense nucleic acids which induce exon skipping for 39 exons were produced by Annemieke Aartsma-Rus, et al., Netherlands (Non Patent Literature 4).

It is considered that approximately 13% of all DMD patients may be treated by skipping the 51st exon (hereinafter referred to as "exon 51"). In recent years, a plurality of reports have been made on the studies where exon 51 in the dystrophin gene was targeted for exon skipping (Patent Literatures 1 to 10 and Non Patent Literatures 3 to 7).

CITATION LIST

Patent Literature

[Patent Literature 1] International Publication WO2015/137409
[Patent Literature 2] International Publication WO2019/241385
[Patent Literature 3] International Publication WO2002/024906
[Patent Literature 4] International Publication WO2004/048570
[Patent Literature 5] International Publication WO2004/083432
[Patent Literature 6] International Publication WO2006/000057

[Patent Literature 7] International Publication WO2010/048586
[Patent Literature 8] International Publication WO2009/054725
[Patent Literature 9] International Publication WO2010/050801
[Patent Literature 10] International Publication WO2010/050802
[Non Patent Literature 1] Monaco A. P. et al., Genomics 2:90-95 (1988)
[Non Patent Literature 2] Matsuo M., Brain and Development 18:167-172 (1996)
[Non Patent Literature 3] Wilton S. D. et al., Molecular Therapy 15:1288-1296 (2007)
[Non Patent Literature 4] Annemieke Aartsma-Rus et al., Neuromuscular Disorders 12:S71-S77 (2002)
[Non Patent Literature 5] Aoki Y. et al., Molecular Therapy 18: 1995-2005 (2010)
[Non Patent Literature 6] Nakano S. et al., Pediatrics International 53: 524-529 (2011)
[Non Patent Literature 7] Echigoya Y et al., Molecular Therapy 25: 2561-2572 (2017)

SUMMARY OF INVENTION

Technical Problem

Under the foregoing circumstances, novel antisense oligomers that induce exon 51 skipping in the dystrophin gene with high efficiency have been desired. Also, antisense oligomers that have excellent properties (e.g., solubility and safety) as medicaments while maintaining an activity to induce exon 51 skipping in the dystrophin gene with high efficiency have been desired.

Solution to Problem

As a result of detailed studies of the technical contents of the above documents and the structure of the dystrophin gene, the present inventors have found that exon 51 skipping in the human dystrophin gene is induced with high efficiency by administering the antisense oligomer having a base sequence represented by any of SEQ ID NOs: 1 to 89 and 91 to 93. As a result of studies, the present inventors have also found that the antisense oligomer has excellent solubility and safety while inducing exon 51 skipping in the human dystrophin gene with high efficiency. Based on this finding, the present inventors have accomplished the present invention.

That is, the present invention is as follows.

[1]

An antisense oligomer which is selected from the group consisting of (a1) to (d1) below:
(a1) an antisense oligomer comprising a base sequence of any of SEQ ID NOs: 1 to 89 and 91 to 93;
(b1) an antisense oligomer which comprises a base sequence having deletion, substitution, insertion and/or addition of 1 to 5 base(s) in the base sequence of any of SEQ ID NOs: 1 to 89 and 91 to 93, and has an activity to induce skipping of exon 51 in the human dystrophin gene;
(c1) an antisense oligomer which comprises a base sequence having at least 80% sequence identity to a base sequence of any of SEQ ID NOs: 1 to 89 and 91 to 93, and has an activity to induce skipping of exon 51 in the human dystrophin gene; and
(d1) an antisense oligomer that hybridizes under stringent conditions to an oligonucleotide consisting of a base sequence complementary to the base sequence of any of SEQ ID NOs: 1 to 89 and 91 to 93, and has an activity to induce skipping of exon 51 in the human dystrophin gene, (except for an antisense oligomer which consists of a base sequence of any of SEQ ID NOs: 90 and 97 to 126) or a pharmaceutically acceptable salt or hydrate thereof.

[2]

An antisense oligomer which is selected from the group consisting of (e) to (h) below:
(e) an antisense oligomer which consists of a base sequence of any of SEQ ID NOs: 1 to 89 and 91 to 93;
(f) an antisense oligomer which consists of a base sequence having deletion and/or substitution of 1 to 5 base(s) in the base sequence of any of SEQ ID NOs: 1 to 89 and 91 to 93, and has an activity to induce skipping of exon 51 in the human dystrophin gene;
(g) an antisense oligomer which consists of a base sequence having at least 80% sequence identity to a base sequence of any of SEQ ID NOs: 1 to 89 and 91 to 93, and has an activity to induce skipping of exon 51 in the human dystrophin gene; and
(h) an antisense oligomer that hybridizes under high stringent conditions to an oligonucleotide consisting of a base sequence complementary to the base sequence of any of SEQ ID NOs: 1 to 89 and 91 to 93, and has an activity to induce skipping of exon 51 in the human dystrophin gene, (except for an antisense oligomer which consists of a base sequence of any of SEQ ID NOs: 90 and 97 to 126) or a pharmaceutically acceptable salt or hydrate thereof

[3]

The antisense oligomer or the pharmaceutically acceptable salt or hydrate thereof according to [1] or [2] above, wherein
the antisense oligomer is
an antisense oligomer which has a nucleotide sequence having at least 90% sequence identity to a base sequence of any of SEQ ID NOs: 1 to 89 and 91 to 93, and has an activity to induce skipping of exon 51 in the human dystrophin gene.

[4]

The antisense oligomer or the pharmaceutically acceptable salt or hydrate thereof according to [1] above, wherein the antisense oligomer is an antisense oligomer which is selected from the group consisting of:
(a2) an antisense oligomer comprising a base sequence of any of SEQ ID NOs: 7, 8, 10, 16, 21, 24, 31, 42, 67 and 76;
(b2) an antisense oligomer which comprises a base sequence having deletion, substitution, insertion and/or addition of 1 to 5 base(s) in the base sequence of any of SEQ ID NOs: 7, 8, 10, 16, 21, 24, 31, 42, 67 and 76, and has an activity to induce skipping of exon 51 in the human dystrophin gene;
(c2) an antisense oligomer which comprises a base sequence having at least 80% sequence identity to a base sequence of any of SEQ ID NOs: 7, 8, 10, 16, 21, 24, 31, 42, 67 and 76, and has an activity to induce skipping of exon 51 in the human dystrophin gene; and
(d2) an antisense oligomer that hybridizes under stringent conditions to an oligonucleotide consisting of a base sequence complementary to the base sequence of any of SEQ ID NOs: 7, 8, 10, 16, 21, 24, 31, 42, 67 and 76, and has an activity to induce skipping of exon 51 in the human dystrophin gene.

[5]

The antisense oligomer or the pharmaceutically acceptable salt or hydrate thereof according to any of [1] to [4] above, wherein the antisense oligomer is an oligonucleotide.

[6]
The antisense oligomer or the pharmaceutically acceptable salt or hydrate thereof according to [5] above, wherein the sugar moiety and/or the phosphate bond moiety of at least one nucleotide constituting the oligonucleotide are/is modified.

[7]
The antisense oligomer or the pharmaceutically acceptable salt or hydrate thereof according to [5] or [6] above, wherein the sugar moiety of at least one nucleotide constituting the oligonucleotide is a ribose in which the 2'-OH group is replaced by any one selected from the group consisting of OR, R, R'OR, SH, SR, $NH_2$, NHR, $NR_2$, $N_3$, CN, F, Cl, Br and I (wherein R is an alkyl or an aryl, and R' is an alkylene).

[8]
The antisense oligomer or the pharmaceutically acceptable salt or hydrate thereof according to any of [5] to [7] above, wherein the phosphate bond moiety of at least one nucleotide constituting the oligonucleotide is any one selected from the group consisting of a phosphorothioate bond, a phosphorodithioate bond, an alkylphosphonate bond, a phosphoramidate bond and a boranophosphate bond.

[9]
The antisense oligomer or the pharmaceutically acceptable salt or hydrate thereof according to any of [1] to [4] above, wherein the antisense oligomer is a morpholino oligomer.

[10]
The antisense oligomer or the pharmaceutically acceptable salt or hydrate thereof according to [9] above, wherein the antisense oligomer is a phosphorodiamidate morpholino oligomer.

[11]
The antisense oligomer or the pharmaceutically acceptable salt or hydrate thereof according to [9] or [10] above, wherein the 5' end is any one of chemical formulae (1) to (3) below:

[Formula 1]

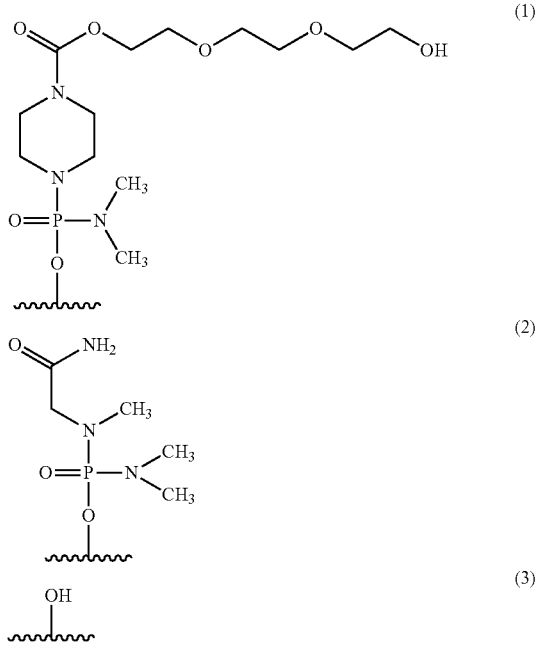

[12]
A pharmaceutical composition for the treatment of muscular dystrophy, comprising the antisense oligomer or the pharmaceutically acceptable salt or hydrate thereof according to any of [1] to [11] above.

[13]
The pharmaceutical composition according to [12] above, further comprising a pharmaceutically acceptable carrier.

[14]
The pharmaceutical composition according to [12] or [13] above for being administered to a patient with muscular dystrophy, wherein the patient is a patient having a mutation that is amenable to exon 51 skipping in the dystrophin gene.

[15]
The pharmaceutical composition according to [14] above, wherein the patient has the dystrophin gene that has at least a frameshift mutation caused by deletion of an exon in the vicinity of exon 51 and in which the amino acid reading frame is corrected by exon 51 skipping.

[16]
The pharmaceutical composition according to [14] or [15] above, wherein the patient has a frameshift mutation caused by deletions of exons 13-50, 29-50, 40-50, 43-50, 45-50, 47-50, 48-50, 49-50, 50, 52, or 52-63 in the dystrophin gene.

[17]
The pharmaceutical composition according to any of [14] to [16] above, wherein the patient is a human.

[18]
Use of the antisense oligomer or the pharmaceutically acceptable salt or hydrate thereof according to any of [1] to [11] above in the manufacture of a medicament for the treatment of muscular dystrophy.

[19]
A method for treatment of muscular dystrophy, which comprises administering to a patient with muscular dystrophy an effective amount of the antisense oligomer or the pharmaceutically acceptable salt or hydrate thereof according to any of [1] to [11] above, or the pharmaceutical composition according to any of [12] to [16] above.

[20]
The method for treatment according to [19] above, wherein the patient is a human.

[21]
The antisense oligomer or the pharmaceutically acceptable salt or hydrate thereof according to any of [1] to [11] above, or the pharmaceutical composition according to any of [12] to [16] above for use in the treatment of muscular dystrophy.

[22]
The antisense oligomer or the pharmaceutically acceptable salt or hydrate thereof, or the pharmaceutical composition according to [21] above, wherein in the Effects of Invention The present invention can provide an antisense oligomer that induces exon 51 skipping in the human dystrophin gene with high efficiency. The present invention can provide an antisense oligomer that has excellent solubility while maintaining an activity to induce exon 51 skipping in the human dystrophin gene with high efficiency. The present invention can further provide an antisense oligomer that has excellent solubility and safety (e.g., having no influence on or being very unlikely to have influence on the functions of the kidney and the liver) while maintaining an activity to induce exon 51 skipping in the human dystrophin gene with high efficiency.

DESCRIPTION OF EMBODIMENTS

Figure 1:
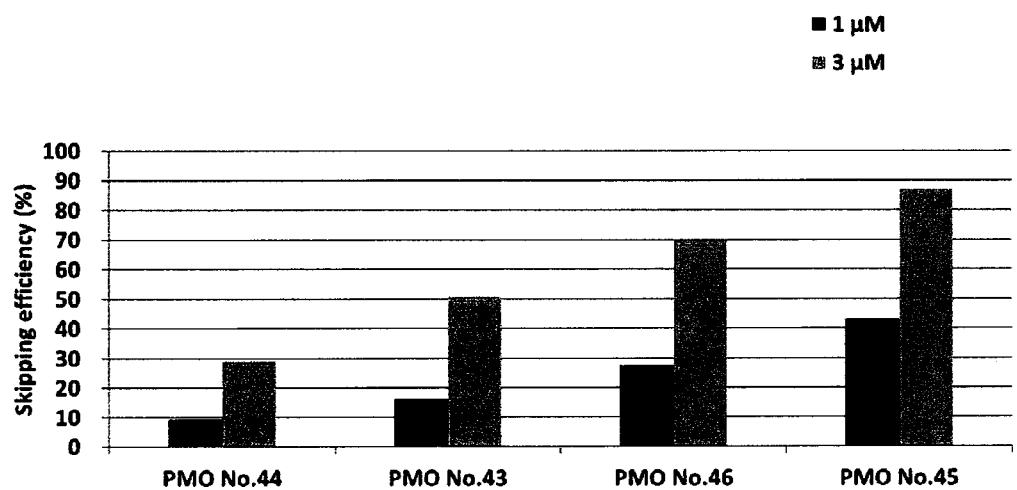
FIG. 1 shows the efficiency of exon 51 skipping in the human dystrophin gene by antisense oligomers of PMO Nos. 43, 44, 45, and 46 in human rhabdomyosarcoma cells (RD cells).
Figure 2:
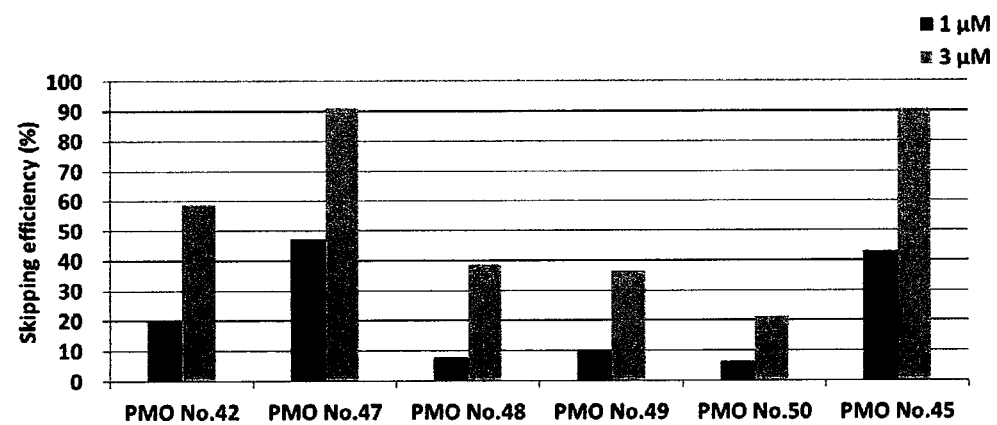
FIG. 2 shows the efficiency of exon 51 skipping in the human dystrophin gene by antisense oligomers of PMO Nos. 42, 45, 47, 48, 49, and 50 in RD cells.
Figure 3:
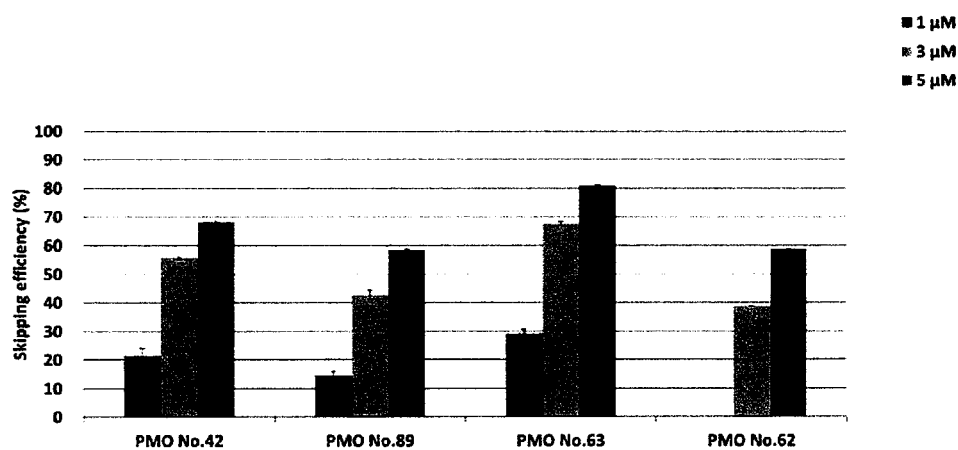
FIG. 3 shows the efficiency of exon 51 skipping in the human dystrophin gene by antisense oligomers of PMO Nos. 42, 62, 63, and 89 in RD cells.
Figure 4:
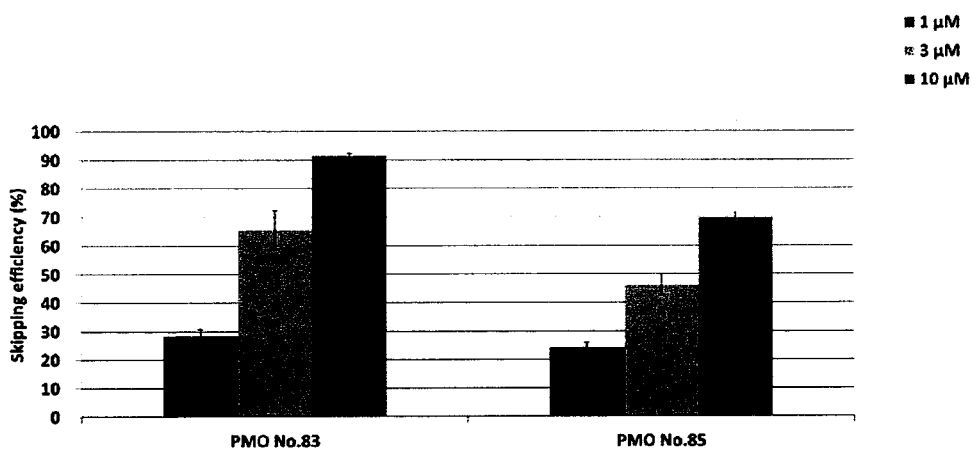
FIG. 4 shows the efficiency of exon 51 skipping in the human dystrophin gene by antisense oligomers of PMO Nos. 83 and 85 in RD cells.
Figure 5:
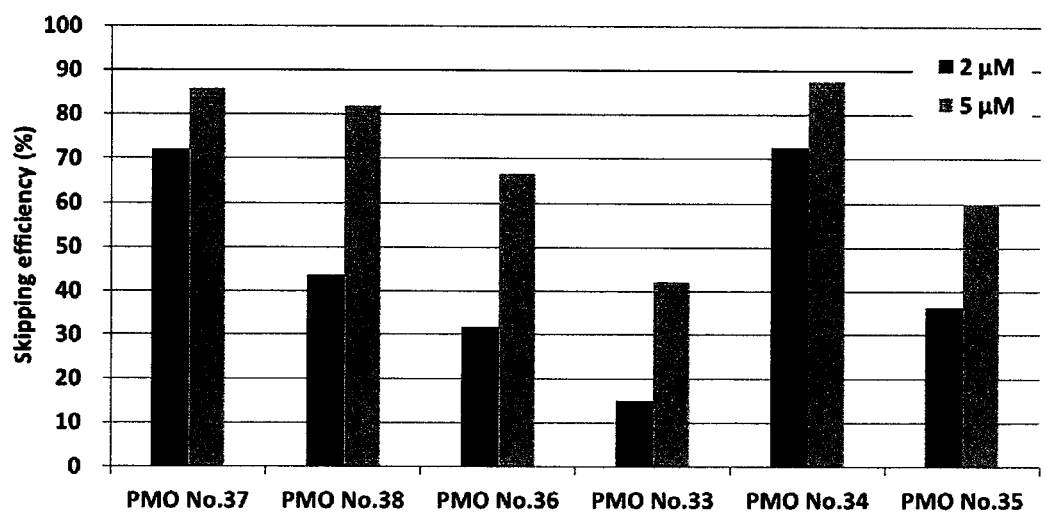
FIG. 5 shows the efficiency of exon 51 skipping in the human dystrophin gene by antisense oligomers of PMO Nos. 33, 34, 35, 36, 37, and 38 in RD cells.
Figure 6:
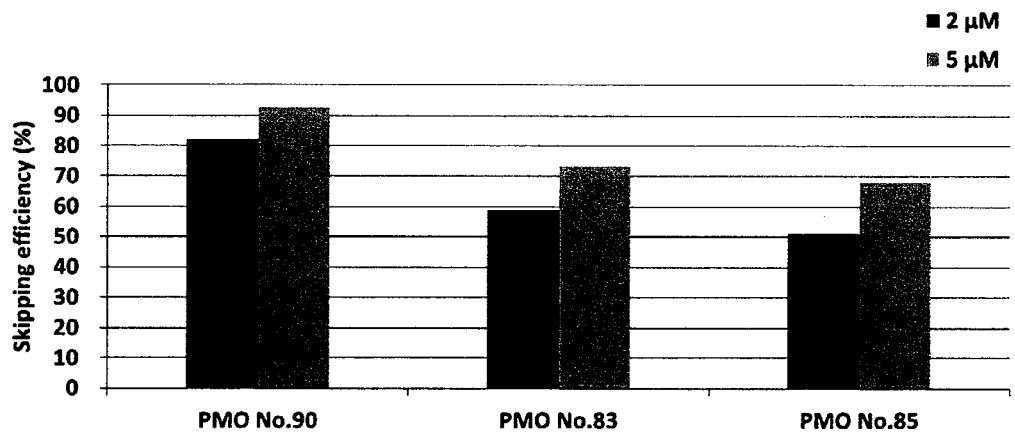
FIG. 6 shows the efficiency of exon 51 skipping in the human dystrophin gene by antisense oligomers of PMO Nos. 83, 85, and 90 in RD cells.
Figure 7:
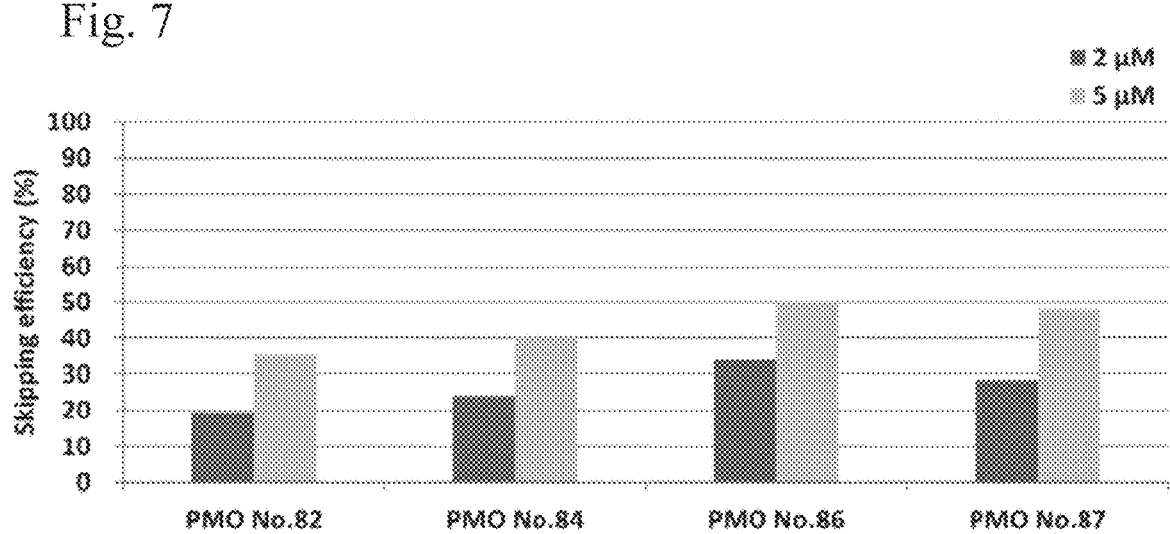
FIG. 7 shows the efficiency of exon 51 skipping in the human dystrophin gene by antisense oligomers of PMO Nos. 82, 84, 86, and 87 in RD cells.
Figure 8:
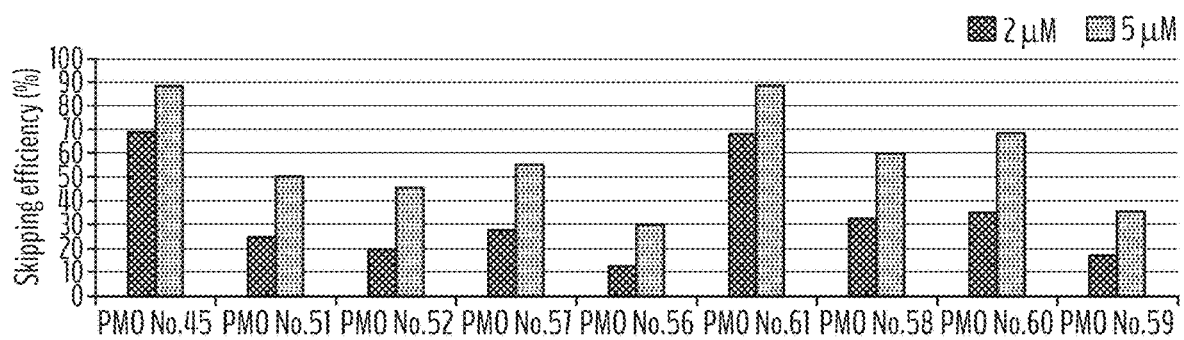
FIG. 8 shows the efficiency of exon 51 skipping in the human dystrophin gene by antisense oligomers of PMO Nos. 45, 51, 52, 56, 57, 58, 59, 60, and 61 in RD cells.
Figure 9:
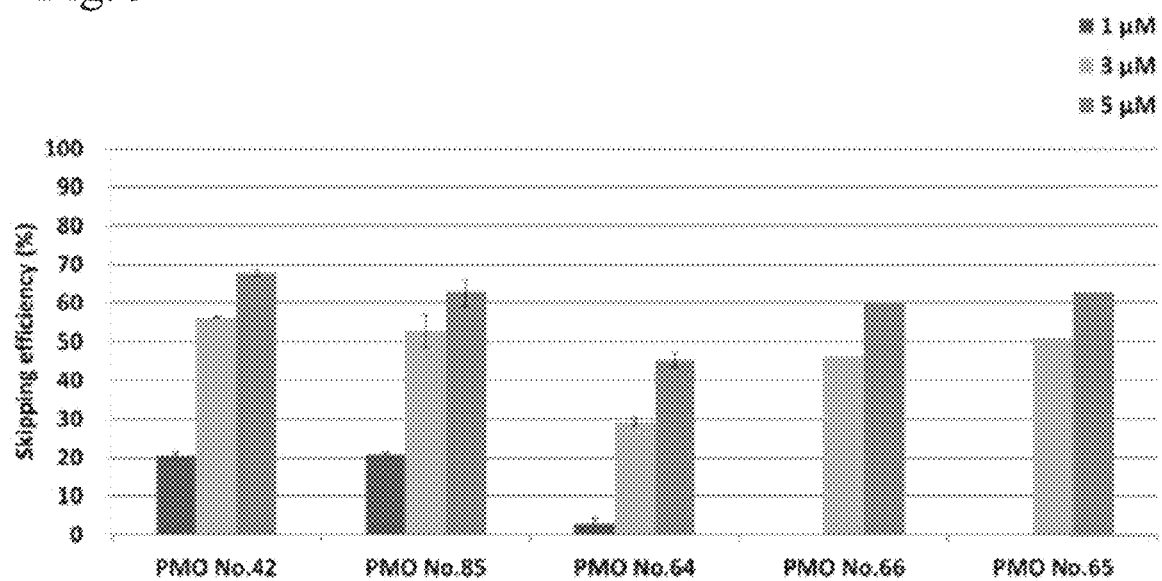
FIG. 9 shows the efficiency of exon 51 skipping in the human dystrophin gene by antisense oligomers of PMO Nos. 42, 64, 65, 66, and 85 in RD cells.
Figure 10:
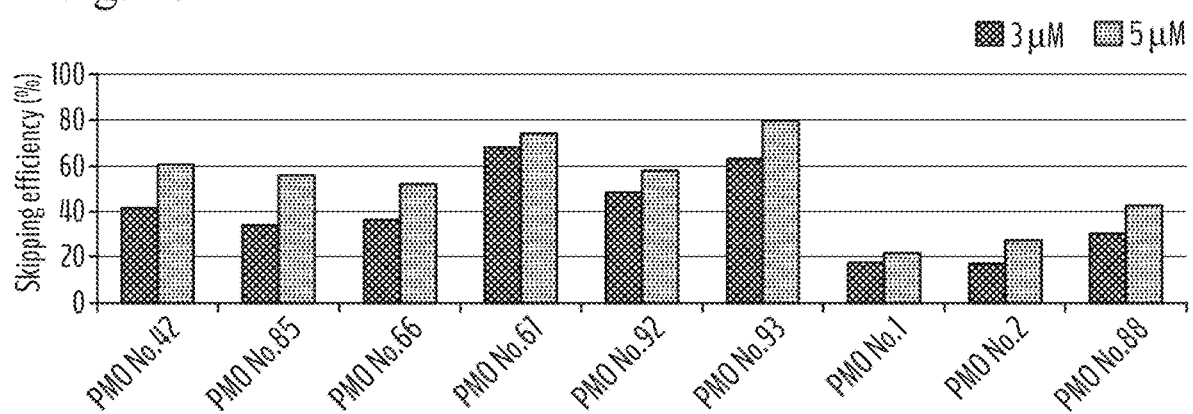
FIG. 10 shows the efficiency of exon 51 skipping in the human dystrophin gene by antisense oligomers of PMO Nos. 1, 2, 42, 66, 67, 85, 88, 92, and 93 in RD cells.
Figure 11:
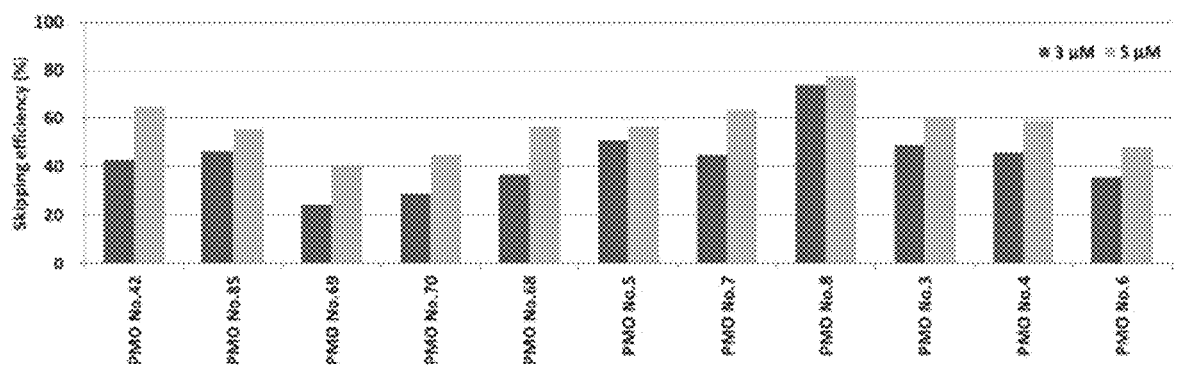
FIG. 11 shows the efficiency of exon 51 skipping in the human dystrophin gene by antisense oligomers of PMO Nos. 3, 4, 5, 6, 7, 8, 42, 68, 69, 70, and 85 in RD cells.
Figure 12:
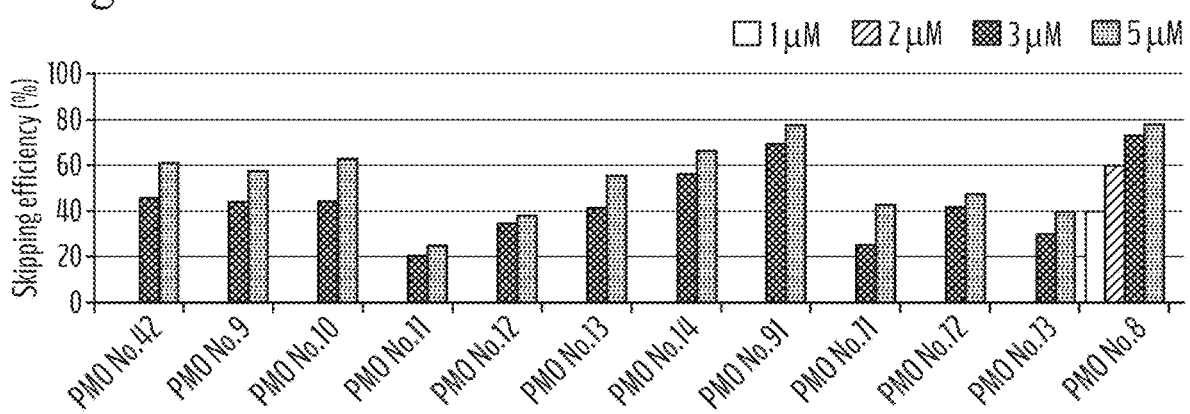
FIG. 12 shows the efficiency of exon 51 skipping in the human dystrophin gene by antisense oligomers of PMO Nos. 8, 9, 10, 11, 12, 13, 14, 42, 71, 72, 73, and 91 in RD cells.
Figure 13:
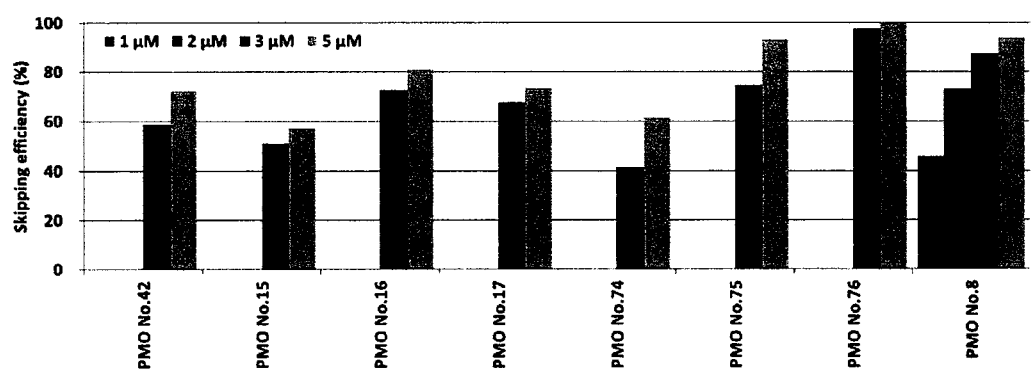
FIG. 13 shows the efficiency of exon 51 skipping in the human dystrophin gene by antisense oligomers of PMO Nos. 8, 15, 16, 17, 42, 74, 75, and 76 in RD cells.
Figure 14:
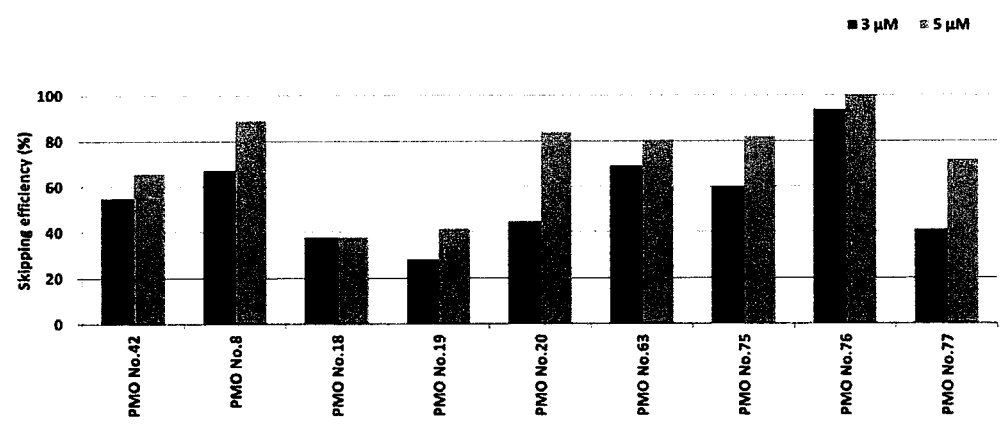
FIG. 14 shows the efficiency of exon 51 skipping in the human dystrophin gene by antisense oligomers of PMO Nos. 8, 18, 19, 20, 42, 63, 75, 76, and 77 in RD cells.
Figure 15:
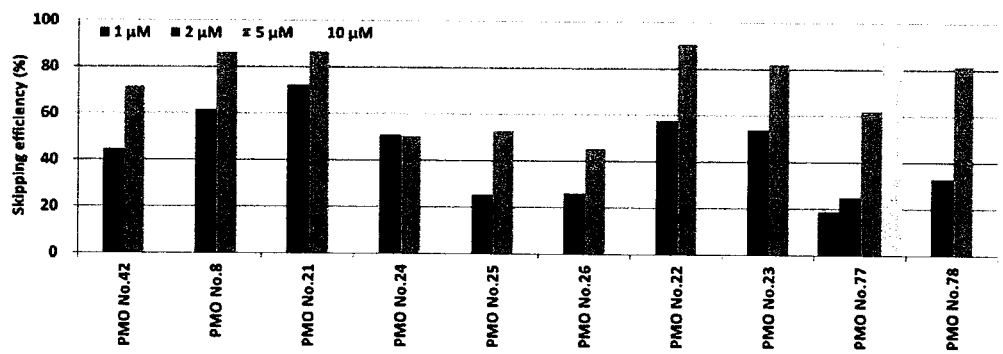
FIG. 15 shows the efficiency of exon 51 skipping in the human dystrophin gene by antisense oligomers of PMO Nos. 8, 21, 22, 23, 24, 25, 26, 42, 77, and 78 in RD cells.
Figure 16:
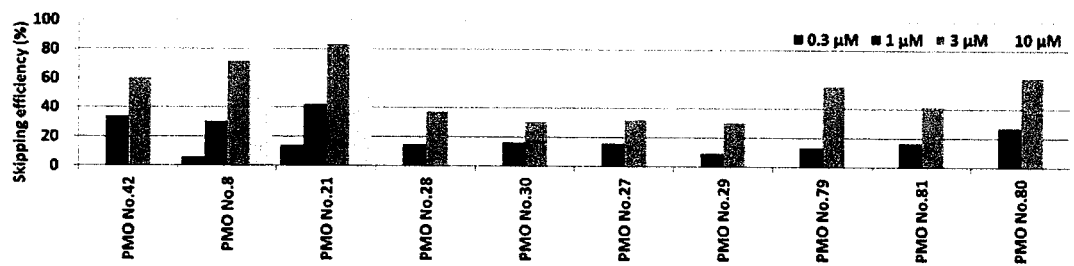
FIG. 16 shows the efficiency of exon 51 skipping in the human dystrophin gene by antisense oligomers of PMO Nos. 8, 21, 27, 28, 29, 30, 42, 79, 80, and 81 in RD cells.
Figure 17:
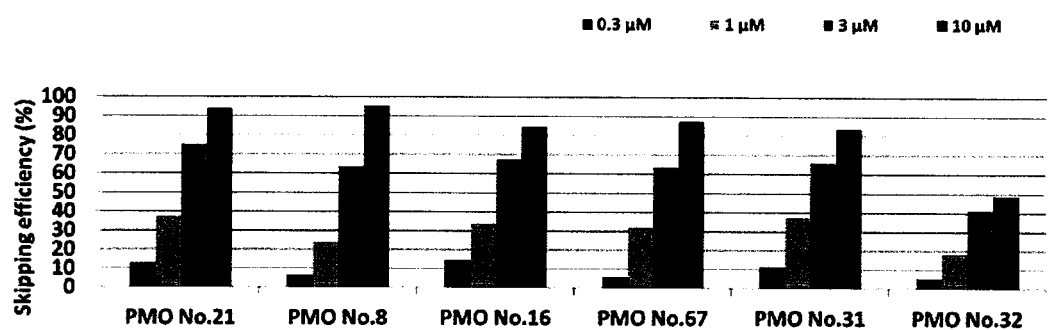
FIG. 17 shows the efficiency of exon 51 skipping in the human dystrophin gene by antisense oligomers of PMO Nos. 8, 16, 21, 31, 32, and 67 in RD cells.
Figure 18:
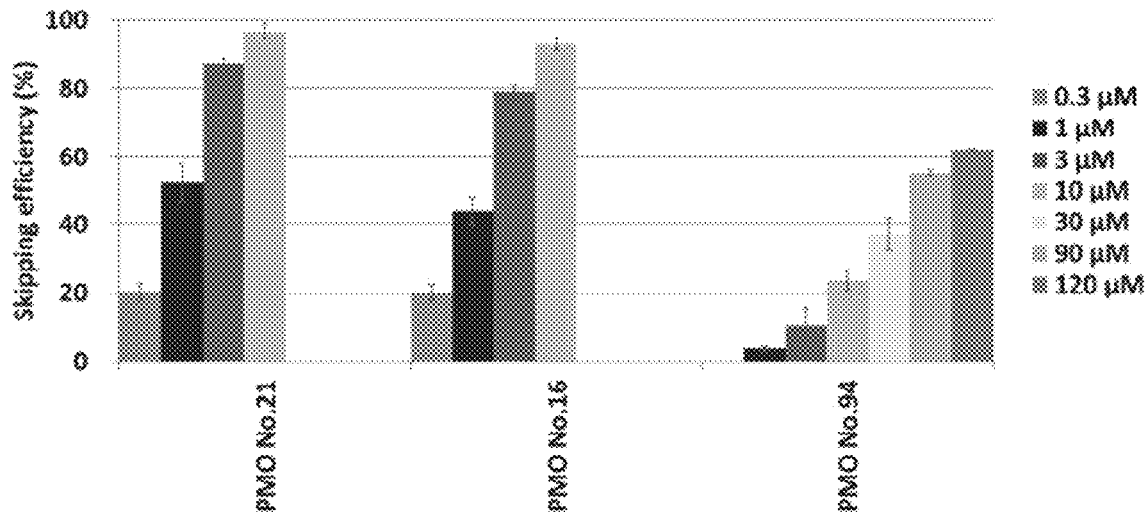
FIG. 18 shows the efficiency of exon 51 skipping in the human dystrophin gene by antisense oligomers of PMO Nos. 16, 21, and 94 in RD cells.

Hereinafter, the present invention is described in detail. The embodiments described below are intended to be presented by way of example merely to describe the invention but not intended to limit the present invention only to the following embodiments. The present invention may be implemented in various ways without departing from the gist of the invention.

1. Antisense Oligomer

The present invention provides an antisense oligomer (hereinafter referred to as the "antisense oligomer of the present invention") which causes skipping of exon 51 in the human dystrophin gene with high efficiency.

[Exon 51 in human dystrophin gene]

In the present invention, the term "gene" includes a genomic gene and also includes cDNA, mRNA precursor, and mRNA. Preferably, the gene is mRNA precursor, i.e., pre-mRNA.

In the human genome, the human dystrophin gene locates at locus Xp21.2. The human dystrophin gene has a size of 2.2 million base pairs and is the largest gene among known human genes. However, the coding regions of the human dystrophin gene are only 14 kb, distributed as 79 exons throughout the human dystrophin gene (Roberts, R G, et al., Genomics, 16: 536-538 (1993); and Koenig, M., et al., Cell 53: 219-228 (1988)). The pre-mRNA, which is the transcript of the human dystrophin gene, undergoes splicing to generate mature mRNA of 14 kb. The base sequence of human wild-type dystrophin gene is known (GenBank Accession No. NM_004006).

A base sequence of exon 51 in the human wild-type dystrophin gene is represented by SEQ ID NO: 127.

[Antisense Oligomer]

The antisense oligomer of the present invention is designed to cause skipping of exon 51 in the human dystrophin gene, thereby modifying the protein encoded by DMD type dystrophin gene into BMD type dystrophin protein. Accordingly, exon 51 in the dystrophin gene that is a target of exon skipping by the antisense oligomer includes both wild type and mutant types.

The antisense oligomer of the present invention is specifically an antisense oligomer which is selected from the group consisting of (a1) to (d1) below.

(a1) an antisense oligomer comprising a base sequence of any of SEQ ID NOs: 1 to 89 and 91 to 93;

(b1) an antisense oligomer which comprises a base sequence having deletion, substitution, insertion and/or addition of 1 to 5, 1 to 4, 1 to 3, 1 to 2, or 1 base(s) in the base sequence of any of SEQ ID NOs: 1 to 89 and 91 to 93, and has an activity to induce skipping of exon 51 in the human dystrophin gene;

(c1) an antisense oligomer which comprises a base sequence having at least 80%, at least 84%, at least 85%, at least 89%, at least 90%, at least 94%, or at least 95% sequence identity to a base sequence of any of SEQ ID NOs: 1 to 89 and 91 to 93, and has an activity to induce skipping of exon 51 in the human dystrophin gene; and (d1) an antisense oligomer that hybridizes under stringent conditions to an oligonucleotide consisting of a base sequence complementary to the base sequence of any of SEQ ID NOs: 1 to 89 and 91 to 93, and has an activity to induce skipping of exon 51 in the human dystrophin gene.

As another embodiment, the antisense oligomer of the present invention is specifically an antisense oligomer which is selected from the group consisting of (e) to (h) below.

(e) an antisense oligomer which consists of a base sequence of any of SEQ ID NOs: 1 to 89 and 91 to 93;

(f) an antisense oligomer which consists of a base sequence having deletion and/or substitution of 1 to 5, 1 to 4, 1 to 3, 1 to 2, or 1 base(s) in the base sequence of any of SEQ ID NOs: 1 to 89 and 91 to 93, and has an activity to induce skipping of exon 51 in the human dystrophin gene;

(g) an antisense oligomer which consists of a base sequence having at least 80%, at least 84%, at least 85%, at least 89%, at least 90%, at least 94%, or at least 95% sequence identity to a base sequence of any of SEQ ID NOs: 1 to 89 and 91 to 93, and has an activity to induce skipping of exon 51 in the human dystrophin gene; and (h) an antisense oligomer that hybridizes under high stringent conditions to an oligonucleotide consisting of a base sequence complementary to the base sequence of any of SEQ ID NOs: 1 to 89 and 91 to 93, and has an activity to induce skipping of exon 51 in the human dystrophin gene.

The antisense oligomer of the present invention is more preferably an antisense oligomer which is selected from the group consisting of (a2) to (d2) below.

(a2) an antisense oligomer comprising a base sequence of any of SEQ ID NOs: 7, 8, 10, 16, 21, 24, 31, 42, 67 and 76;

(b2) an antisense oligomer which comprises a base sequence having deletion, substitution, insertion and/or addition of 1 to 5 base(s) in the base sequence of any of SEQ ID NOs: 7, 8, 10, 16, 21, 24, 31, 42, 67 and 76, and has an activity to induce skipping of exon 51 in the human dystrophin gene;

(c2) an antisense oligomer which comprises a base sequence having at least 80% sequence identity to a base sequence of any of SEQ ID NOs: 7, 8, 10, 16, 21, 24, 31, 42, 67 and 76, and has an activity to induce skipping of exon 51 in the human dystrophin gene; and (d2) an antisense oligomer that hybridizes under stringent conditions to an oligonucleotide consisting of a base sequence complementary to the base sequence of any of SEQ ID NOs: 7, 8, 10, 16, 21, 24, 31, 42, 67 and 76, and has an activity to induce skipping of exon 51 in the human dystrophin gene.

The antisense oligomers of (b1) to (d1), (f) to (h), and (b2) to (d2) are mutants of the antisense oligomers of (a1), (e), and (a2), respectively, in particular and are intended to correspond to mutations (e.g., polymorphism) of the dystrophin gene of the patients.

However, the antisense oligomer of the present invention excludes (does not include) antisense oligomers consisting of the following base sequences described in International Publication WO2015/137409.

TABLE 1

| Sequence | SEQ ID NO |
|---|---|
| CGGTAAGTTCTGTCCTCAAGGAAGATGGCA | 90 |
| CTCATACCTTCTGCTTCAAGGAAGATGGCA | 97 |
| CTCCAACATCAAGGAAGATGGCATTTCTAG | 98 |
| AACATCAAGGAAGATGGCATT | 99 |
| TCCAACATCAAGGAAGATGGC | 100 |
| ACCTCCAACATCAAGGAAGAT | 101 |
| GAGUAACAGUCUGAGUAGGAG | 102 |
| UGUGUCACCAGAGUAACAGUC | 103 |
| AACCACAGGUUGUGUCACCAG | 104 |
| UUUCCUUAGUAACCACAGGUU | 105 |
| GAGAUGGCAGUUUCCUUAGUA | 106 |
| UUCUAGUUUGGAGAUGGCAGU | 107 |
| AAGAUGGCAUUUCUAGUUUGG | 108 |
| AACAUCAAGGAAGAUGGCAUU | 109 |
| AGGUACCUCCAACAUCAAGGA | 110 |
| CUGCCAGAGCAGGUACCUCCA | 111 |
| CGGUUGAAAUCUGCCAGAGCA | 112 |
| UGUCCAAGCCCGGUUGAAAUC | 113 |
| CGGUAAGUUCUGUCCAAGCCC | 114 |
| GAAAGCCAGUCGGUAAGUUCU | 115 |
| AUCAAGCAGAGAAAGCCAGUC | 116 |
| UUAUAACUUGAUCAAGCAGAG | 117 |
| CUCUGUGAUUUUAUAACUUGA | 118 |
| CACCAUCACCCUCUGUGAUUU | 119 |
| CAAGGUCACCCACCAUCACCC | 120 |
| UUGAUAUCCUCAAGGUCACCC | 121 |
| GAUCAUCUCGUUGAUAUCCUC | 122 |
| UCUGCUUGAUGAUCAUCUCGU | 123 |
| GGCAUUUCUAGUUUGGAGAUG | 124 |
| CAAGGAAGAUGGCAUUUCUAG | 125 |
| CCUCCAACAUCAAGGAAGAUG | 126 |

As used herein, the term "antisense oligomer that hybridizes under stringent conditions" refers to, for example, an antisense oligomer obtained by colony hybridization, plaque hybridization, Southern hybridization or the like, using as a probe all or part of an oligonucleotide consisting of a base sequence complementary to the base sequence of, e.g., any of SEQ ID NOs: 1 to 89 and 91 to 93. The hybridization method which may be used includes methods described in, for example, "Sambrook & Russell, Molecular Cloning: A Laboratory Manual Vol. 3, Cold Spring Harbor, Laboratory Press 2001," "Ausubel, Current Protocols in Molecular Biology, John Wiley & Sons 1987-1997," etc.

As used herein, the term "stringent conditions" may be any of low stringent conditions, moderate stringent conditions or high stringent conditions. The term "low stringent condition" is, for example, 5×SSC, 5×Denhardt's solution, 0.5% SDS, 50% formamide at 32° C. The term "moderate stringent condition" is, for example, 5×SSC, 5×Denhardt's solution, 0.5% SDS, 50% formamide at 42° C., or 5×SSC, 1% SDS, 50 mM Tris-HCl (pH 7.5), 50% formamide at 42° C. The term "high stringent condition" is, for example, (1) 5×SSC, 5×Denhardt's solution, 0.5% SDS, 50% formamide at 50° C., (2) 0.2×SSC, 0.1% SDS at 60° C., (3) 0.2×SSC, 0.1% SDS at 62° C., (4) 0.2×SSC, 0.1% SDS at 65° C., or (5) 0.1×SSC, 0.1% SDS at 65° C., but is not limited thereto. Under these conditions, antisense oligomers with higher sequence identity are expected to be obtained efficiently at higher temperatures. Multiple factors are involved in hybridization stringency including temperature, probe concentration, probe length, ionic strength, time, salt concentration and others, and those skilled in the art may appropriately select these factors to achieve similar stringency. Herein, the term "sequence identity" refers to identity over the whole ranges of base sequences to be compared between a pair of two certain nucleic acids and is indicated by the ratio (%) of matched bases in the optimum alignment of the base sequences produced using a mathematical algorithm known in the technical field of the present invention. For example, an antisense oligomer consisting of a base sequence having at least "80% sequence identity" to an antisense oligomer consisting of a 20-base sequence means an antisense oligomer having 16 or more bases identical to the 20-base antisense oligomer.

The sequence identity may be determined using FASTA (Science 227 (4693): 1435-1441, (1985)) or algorithm BLAST (Basic Local Alignment Search Tool) by Karlin and Altschul (Proc. Natl. Acad. Sci. USA 872264-2268, 1990; and Proc Natl Acad Sci USA 90: 5873, 1993). Programs called blastn, blastx, tblastn and tblastx based on the BLAST algorithm have been developed (Altschul S F, et al: J. Mol. Biol. 215: 403, 1990). When a base sequence is analyzed using blastn, the parameters are, for example, score=100 and wordlength=12. When BLAST and Gapped BLAST programs are used, the default parameters for each program are employed.

When commercially available kits are used for hybridization, for example, an Alkphos Direct Labelling and Detection System (GE Healthcare) may be used. In this case, according to the attached protocol to the kit, after incubation with a labeled probe overnight, the membrane is washed with a primary wash buffer containing 0.1% (w/v) SDS at 55° C., thereby enabling to detect hybridized antisense oligomer. Alternatively, when the probe is labeled with digoxigenin (DIG) using a commercially available reagent (e.g., a PCR Labelling Mix (Roche Diagnostics), etc.) in producing a probe based on all or part of the complementary sequence to the base sequence of any of SEQ ID NOs: 1 to 89 and 91 to 93, hybridization can be detected with a DIG Nucleic Acid Detection Kit (Roche Diagnostics).

In addition to the antisense oligomer described above, other antisense oligomer that can hybridize include antisense oligomers having 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, and 99.9% or higher sequence identity to the base sequence of any of SEQ ID NOs: 1 to 89 and 91 to 93, as calculated by homology search software such as FASTA and BLAST using the default parameters.

The term "induce skipping of the exon 51 in the human dystrophin gene" is intended to mean that by binding of the antisense oligomer of the present invention to the site corresponding to exon 51 and/or its adjacent intron of the transcript (e.g., pre-mRNA) of the human dystrophin gene, exclusion of exon 51 occurs and, for example, the base sequence corresponding to the 5' end of exon 53 is connected to the base sequence corresponding to the 3' end of exon 50 in DMD patients with deletion of exon 52 when the transcript undergoes splicing, thus resulting in formation of mature mRNA which is free of codon frame shift.

Thus, DMD patients having a mutation that is amenable to exon 51 skipping in the dystrophin gene can be treated by exon 51 skipping. Examples of such DMD patients include DMD patients who have the dystrophin gene that has at least a frameshift mutation caused by deletion of an exon in the vicinity of exon 51 and in which the amino acid reading frame is corrected by exon 51 skipping, and more specifically include DMD patients having a frameshift mutation caused by deletions of exons 13-50, 29-50, 40-50, 43-50, 45-50, 47-50, 48-50, 49-50, 50, 52, 52-63, etc. in the dystrophin gene.

Herein, the term "binding" described above is intended to mean that when the antisense oligomer of the present invention is mixed with the transcript of human dystrophin gene, both hybridize with each other under physiological conditions to form a double strand nucleic acid. The term "under physiological conditions" refers to conditions set to mimic the in vivo environment in terms of pH, salt composition, and temperature. The conditions are, for example, 25 to 40° C., preferably 37° C., pH 5 to 8, preferably pH 7.4 and 150 mM of sodium chloride concentration.

Whether the skipping of exon 51 in the human dystrophin gene is caused or not can be confirmed by introducing the antisense oligomer of the present invention into a dystrophin-expressing cell (e.g., human rhabdomyosarcoma cells), amplifying the region surrounding exon 51 of mRNA of the human dystrophin gene from the total RNA of the dystrophin-expressing cell by RT-PCR and performing nested PCR or sequence analysis on the PCR amplified product. The skipping efficiency ES (%) can be determined as follows. The mRNA for the human dystrophin gene is collected from test cells; and in the mRNA, the polynucleotide level of the band showing that exon 51 is skipped (the polynucleotide level "A") and the polynucleotide level of the band showing that exon 51 is not skipped (the polynucleotide level "B") are measured. Using these measurement values of "A" and "B," the efficiency is calculated by the following equation (1). For calculation of the skipping efficiency, International Publication WO2012/029986 may be referred.

$$ES = 100 \times A/(A+B) \tag{1}$$

Preferably, the antisense oligomer of the present invention cause skipping of exon 51 with the efficiency of 10% or higher, 20% or higher, 30% or higher, 40% or higher, 50% or higher, 60% or higher, 70% or higher, 80% or higher, and 90% or higher.

The antisense oligomer of the present invention preferably has high solubility in physiological saline. The antisense oligomer having high solubility in physiological saline, unlike an antisense oligomer having low solubility therein, is very unlikely to precipitate in a preparation during preservation and make the preparation no longer usable, and is also very unlikely to precipitate in a salt-containing infusion fluid used and make the infusion fluid no longer usable. Furthermore, the antisense oligomer having high solubility in physiological saline is unlikely to precipitate and is therefore also very unlikely to exhibit toxicity when administered (Bulletin of Osaka University of Pharmaceutical Sciences 1, 91-99 (2007)). Thus, the antisense oligomer having high solubility in physiological saline is very highly useful as an active ingredient for medicaments.

The solubility in physiological saline is preferably equal to or higher than 20 mg/mL, more preferably equal to or higher than 30 mg/mL, much more preferably equal to or higher than 40 mg/mL, and particularly preferably equal to or higher than 50 mg/mL. The solubility in physiological saline of the antisense oligomer can be evaluated by dissolving the antisense oligomer at an intended concentration in physiological saline, and visually confirming the presence or absence of precipitation after a given time.

The antisense oligomer preferably has high safety as an active ingredient for medicaments. The safety can be evaluated, for example, by using an aspartate aminotransferase (AST) value, an alanine aminotransferase (ALT) value, a blood urea nitrogen (BUN) value, and a creatinine value as indexes in blood after administration of the antisense oligomer. The AST value is elevated when disorder occurs in the liver. The ALT value is elevated when the liver has a problem. The BUN value is elevated when the functions of the kidney decline. The creatinine value tends to be elevated when the glomerular filtration function of the kidney declines. Therefore, the influence of the antisense oligomer on the functions of the kidney and the liver can be evaluated by using these values as indexes.

Specifically, the antisense oligomer is administered to, for example, a healthy mouse, and then, its AST value, ALT value, BUN value and creatinine value in blood are measured and subjected to a statistically significant difference test. When significant elevation is seen in the obtained values compared with measurement values of a control group (vehicle administration or untreated group), the values are determined as outliers. Thus, the administered antisense oligomer can be confirmed to have influence on or to be likely to have influence on the functions of the kidney and the liver. On the other hand, when no such significant elevation is seen, the administered antisense oligomer can be confirmed to have no influence on or to be unlikely to have influence on the functions of the kidney and the liver. Alternatively, when a specific rate of elevation, specifically, for example, 30% or more elevation, is seen in the obtained values compared with the measurement values of the control group, the values may be determined as outliers.

The antisense oligomer of the present invention includes, for example, an oligonucleotide, morpholino oligomer or peptide nucleic acid (PNA) oligomer, having a length of 16, 17, 18, 19, 20, 21, 22, 23, 24, 25, 26, 27, 28, 29, 30, 31, 32, 33, 34, or 35 bases. The length of the antisense oligomer is preferably from 20 to 30 bases, from 20 to 29 bases, from 22 to 30 bases, from 22 to 29 bases or from 25 to 29 bases, more preferably from 22 to 30 bases, from 22 to 29 bases or from 25 to 29 bases, and morpholino oligomers are preferred.

The oligonucleotide described above (hereinafter referred to as "the oligonucleotide of the present invention") is the antisense oligomer of the present invention composed of nucleotides as constituent units. Such nucleotides may be any of ribonucleotides, deoxyribonucleotides and modified nucleotides.

The modified nucleotide refers to one having fully or partly modified nucleobases, sugar moieties and/or phosphate bond moieties, which constitute the ribonucleotide or deoxyribonucleotide.

In the present invention, the nucleobase includes, for example, adenine, guanine, hypoxanthine, cytosine, thymine, uracil, and modified bases thereof. Examples of such modified bases include, but not limited to, pseudouracil, 3-methyluracil, dihydrouracil, 5-alkylcytosines (e.g., 5-methylcytosine), 5-alkyluracils (e.g., 5-ethyluracil), 5-halouracils (5-bromouracil), 6-azapyrimidine, 6-alkylpyrimidines (6-methyluracil), 2-thiouracil, 4-thiouracil, 4-acetylcytosine, 5-(carboxyhydroxymethyl) uracil, 5'-carboxymethylaminomethyl-2-thiouracil, 5-carboxymethylaminomethyluracil, 1-methyladenine, 1-methylhypoxanthine, 2,2-dimethylguanine, 3-methylcytosine, 2-methyladenine, 2-methylguanine, N6-methyladenine, 7-methylguanine, 5-methoxyaminomethyl-2-thiouracil, 5-methylaminomethyluracil, 5-methylcarbonylmethyluracil, 5-methyloxyuracil, 5-methyl-2-thiouracil, 2-methylthio-N6-isopentenyladenine, uracil-5-oxyacetic acid, 2-thiocytosine, purine, 2,6-diaminopurine, 2-aminopurine, isoguanine, indole, imidazole, xanthine, etc.

Modification of the sugar moiety may include, for example, modifications at the 2'-position of ribose and modifications of the other positions of the sugar. The modification at the 2'-position of ribose includes a modification replacing the 2'-OH of ribose with OR, R, R'OR, SH, SR, $NH_2$, NHR, $NR_2$, $N_3$, CN, F, Cl, Br or I, wherein R represents an alkyl or an aryl, and R' represents an alkylene.

The modification for the other positions of the sugar includes, for example, replacement of O at the 4' position of ribose or deoxyribose with S, bridging between 2' and 4' positions of the sugar, e.g., LNA (locked nucleic acid) or ENA (2'-O,4'-C-ethylene-bridged nucleic acids), but is not limited thereto.

A modification of the phosphate bond moiety includes, for example, a modification of replacing phosphodiester bond with phosphorothioate bond, phosphorodithioate bond, alkyl phosphonate bond, phosphoramidate bond or boranophosphate bond (Enya et al: Bioorganic & Medicinal Chemistry, 2008, 18, 9154-9160) (cf., e.g., Japan Domestic Re-Publications of PCT Application Nos. 2006/129594 and 2006/038608).

In this invention, the alkyl includes preferably a straight or branched alkyl having 1 to 6 carbon atoms. Specific examples include methyl, ethyl, n-propyl, isopropyl, n-butyl, isobutyl, sec-butyl, tert-butyl, n-pentyl, isopentyl, neopentyl, tert-pentyl, n-hexyl, and isohexyl. The alkyl may optionally be substituted. Examples of such substituents are a halogen, an alkoxy, cyano, and nitro. The alkyl may be substituted with 1 to 3 substituents.

In this invention, the cycloalkyl includes preferably a cycloalkyl having 5 to 12 carbon atoms. Specific examples include cyclopentyl, cyclohexyl, cycloheptyl, cyclooctyl, cyclodecyl, and cyclododecyl.

In this invention, the halogen includes fluorine, chlorine, bromine, and iodine.

The alkoxy includes a straight or branched alkoxy having 1 to 6 carbon atoms such as methoxy, ethoxy, n-propoxy, isopropoxy, n-butoxy, isobutoxy, sec-butoxy, tert-butoxy, n-pentyloxy, isopentyloxy, n-hexyloxy, isohexyloxy, etc. Among others, an alkoxy having 1 to 3 carbon atoms is preferred.

In this invention, the aryl includes preferably an aryl having 6 to 10 carbon atoms. Specific examples include phenyl, α-naphthyl, and β-naphthyl. Among others, phenyl is preferred. The aryl may optionally be substituted. Examples of such substituents are an alkyl, a halogen, an alkoxy, cyano, and nitro. The aryl may be substituted with one to three of such substituents.

In this invention, the alkylene includes preferably a straight or branched alkylene having 1 to 6 carbon atoms.

Specific examples include methylene, ethylene, trimethylene, tetramethylene, pentamethylene, hexamethylene, 2-(ethyl) trimethylene, and 1-(methyl) tetramethylene.

In this invention, the acyl includes a straight or branched alkanoyl or aroyl. Examples of the alkanoyl include formyl, acetyl, 2-methylacetyl, 2,2-dimethylacetyl, propionyl, butyryl, isobutyryl, pentanoyl, 2,2-dimethylpropionyl, hexanoyl, etc. Examples of the aroyl include benzoyl, toluoyl, and naphthoyl. The aroyl may optionally be substituted at substitutable positions and may be substituted with an alkyl(s).

The oligonucleotide of the present invention is preferably the antisense oligomer of the present invention comprising a constituent unit represented by general formula below wherein the —OH group at position 2' of ribose is substituted with methoxy and the phosphate bond moiety is a phosphorothioate bond:

[Formula 2]

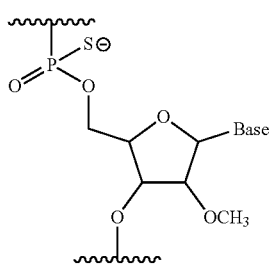

wherein Base represents a nucleobase.

The oligonucleotide of the present invention may be easily synthesized using various automated synthesizer (e.g., AKTA oligopilot plus 10/100 (GE Healthcare)). Alternatively, the synthesis may also be entrusted to a third-party organization (e.g., Promega Inc., Takara Co., or Japan Bio Service Co.), etc.

The morpholino oligomer of the present invention is the antisense oligomer of the present invention comprising the constituent unit represented by general formula below:

[Formula 3]

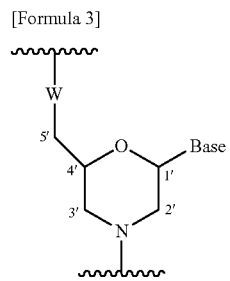

wherein Base has the same meaning as defined above, and W represents a group shown by any one of the following groups:

[Formula 4]

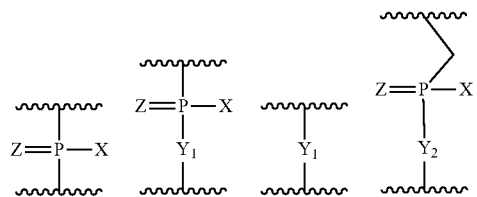

wherein X represents —CH$_2$R$^1$, —O—CH$_2$R$^1$, —S—CH$_2$R$^1$, —NR$^2$R$^3$ or F;
R$^1$ represents H or an alkyl;
R$^2$ and R$^3$, which may be the same or different, each represents H, an alkyl, a cycloalkyl or an aryl;
Y$_1$ represents O, S, CH$_2$ or NR$^1$;
Y$_2$ represents O, S or NR$^1$;
Z represents O or S.

Examples of morpholino monomer compounds that are used in synthesis of the morpholino oligomer of the present invention include, but not limited to, morpholino monomer compound (A), morpholino monomer compound (C), morpholino monomer compound (T), and morpholino monomer compound (G) described in the table below.

TABLE 2

| Morpholino monomer compound (A) | Morpholino monomer compound (C) | Morpholino monomer compound (T) | Morpholino monomer compound (G) |
| --- | --- | --- | --- |

The morpholino oligomer is preferably an oligomer comprising a constituent unit represented by general formula below (phosphorodiamidate morpholino oligomer (hereinafter referred to as "PMO")).

[Formula 5]

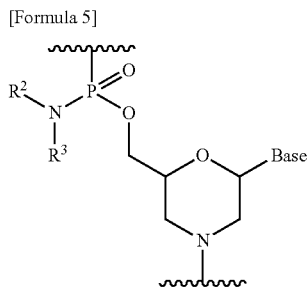

wherein Base, $R^2$ and $R^3$ have the same meaning as defined above.

The morpholino oligomer of the present invention comprises one where all or part of nucleobases, morpholine ring moieties, phosphate bond moieties, 3'-end and/or 5'-end which constitute the morpholino oligomer are modified.

A modification of the phosphate bond moiety includes, for example, a modification of replacing with phosphorodiamidate bond, phosphorothioate bond, phosphorodithioate bond, alkylphosphonate bond, phosphoramidate bond, and boranophosphate bond (Enya et al: Bioorganic & Medicinal Chemistry, 2008, 18, 9154-9160)(cf., e.g., Japan Domestic Re-Publications of PCT Application Nos. 2006/129594 and 2006/038608).

The morpholino oligomer may be produced in accordance with, e.g., WO 1991/009033 or WO 2009/064471. In particular, PMO can be produced by the procedure described in WO 2009/064471 or produced by the process shown below.
[Method for producing PMO]
An embodiment of PMO includes, for example, the compound represented by general formula (I) below (hereinafter PMO (I)).

[Formula 6]

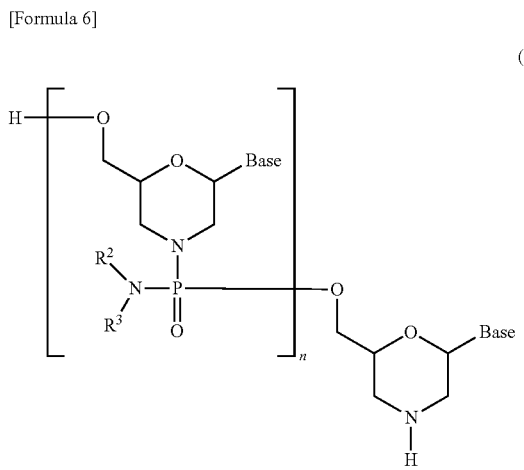

(I)

wherein each Base, $R^2$ and $R^3$ have the same meaning as defined above; and n is a given integer of 1 to 99, preferably a given integer of 19 to 29, 19 to 28, 21 to 29, 21 to 28 or 24 to 28, more preferably 21 to 29, 21 to 28 or 24 to 28.

PMO (I) can be produced in accordance with a known method, for example, can be produced by performing the procedures in the following steps.

The compounds and reagents used in the steps below are not particularly limited so long as they are commonly used to prepare PMO.

Also, the following steps can all be carried out by the liquid phase method or the solid phase method (by manually or using commercially available solid phase automated synthesizers). In producing PMO by the solid phase method, it is preferable to use automated synthesizers in view of simple operation procedures and accurate synthesis.

(1) Step A:

The compound represented by general formula (II) below (hereinafter referred to as Compound (II)) is reacted with an acid to prepare the compound represented by general formula (III) below (hereinafter referred to as Compound (III)):

[Formula 7]

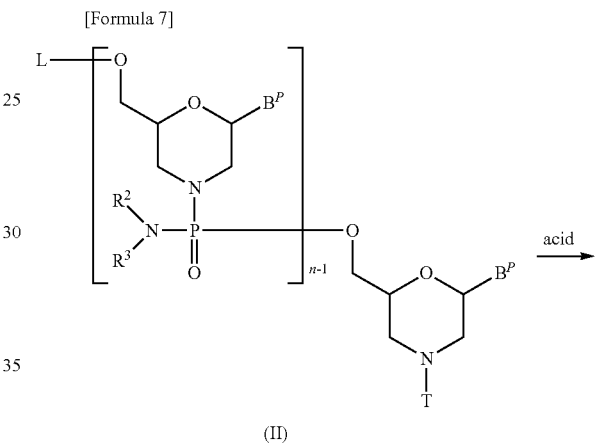

(II)

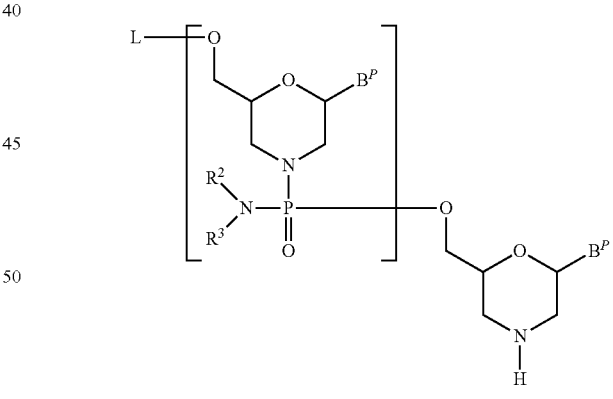

(III)

wherein n, $R^2$ and $R^3$ have the same meaning as defined above;

each $B^P$ independently represents a nucleobase which may optionally be protected;

T represents trityl, monomethoxytrityl or dimethoxytrityl; and,

L represents hydrogen, an acyl or a group represented by general formula (IV) below (hereinafter referred to as group (IV)).

[Formula 8]

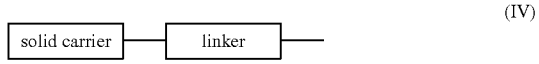
(IV)

The "nucleobase" for $B^P$ includes the same "nucleobase" as in Base, provided that the amino group or hydroxy group in the nucleobase shown by $B^P$ may be protected.

Such protective group for amino group is not particularly limited so long as it is used as a protective group for nucleic acids. Specific examples include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl, and (dimethylamino)methylene. Specific examples of the protective group for the hydroxy group include 2-cyanoethyl, 4-nitrophenethyl, phenylsulfonylethyl, methylsulfonylethyl, trimethylsilylethyl, phenyl, which may be substituted by 1 to 5 electron-withdrawing group at optional substitutable positions, diphenylcarbamoyl, dimethylcarbamoyl, diethylcarbamoyl, methylphenylcarbamoyl, 1-pyrolidinylcarbamoyl, morpholinocarbamoyl, 4-(tert-butylcarboxy) benzyl, 4-[(dimethylamino)carboxy] benzyl, and 4-(phenylcarboxy)benzyl (cf., e.g., WO 2009/064471).

The "solid carrier" is not particularly limited so long as it is a carrier usable for the solid phase reaction of nucleic acids. It is desired for the solid carrier to have the following properties: e.g., (i) it is sparingly soluble in reagents that can be used for the synthesis of morpholino nucleic acid derivatives (e.g., dichloromethane, acetonitrile, tetrazole, N-methylimidazole, pyridine, acetic anhydride, lutidine, trifluoroacetic acid); (ii) it is chemically stable to the reagents that can be used for the synthesis of morpholino nucleic acid derivatives; (iii) it can be chemically modified; (iv) it can be charged with desired morpholino nucleic acid derivatives; (v) it has a strength sufficient to withstand high pressure through treatments; and (vi) it has a certain particle diameter range and distribution. Specifically, swellable polystyrene (e.g., aminomethyl polystyrene resin 1% divinilbenzene crosslinked (200-400 mesh) (2.4-3.0 mmol/g) (Tokyo Chemical Industry), Aminomethylated Polystyrene Resin-HCl [divinylbenzene 1%, 100-200 mesh] (Peptide Institute, Inc.)), non-swellable polystyrene (e.g., Primer Support (GE Healthcare)), PEG chain-attached polystyrene (e.g., $NH_2$-PEG resin (Watanabe Chemical Co.), TentaGel resin), controlled pore glass (CPG) (manufactured by, e.g., CPG), oxalyl-controlled pore glass (cf., e.g., Alul et al., Nucleic Acids Research, Vol. 19, 1527 (1991)), TentaGel support-aminopolyethylene glycol-derivatized support (e.g., Wright et al., cf., Tetrahedron Letters, Vol. 34, 3373 (1993)), and a copolymer of Poros-polystyrene/divinylbenzene.

A "linker" which can be used is a known linker generally used to connect nucleic acids or morpholino nucleic acid derivatives. Examples include 3-aminopropyl, succinyl, 2,2'-diethanolsulfonyl, and a long chain alkyl amino (LCAA).

This step can be performed by reacting Compound (II) with an acid.

The "acid" which can be used in this step includes, for example, trifluoroacetic acid, dichloroacetic acid, and trichloroacetic acid. The amount of acid used is appropriately in a range of, for example, 0.1 mol equivalent to 1000 mol equivalents for 1 mol of Compound (II), preferably in a range of 1 mol equivalent to 100 mol equivalents for 1 mol of Compound (II).

An organic amine can be used in combination with the acid described above. The organic amine is not particularly limited and includes, for example, triethylamine. The amount of the organic amine used is appropriately in a range of, e.g., 0.01 mol equivalent to 10 mol equivalents, and preferably in a range of 0.1 mol equivalent to 2 mol equivalents, for 1 mol of the acid.

When a salt or mixture of the acid and the organic amine is used in this step, the salt or mixture includes, for example, a salt or mixture of trifluoroacetic acid and triethylamine, and more specifically, a mixture of 1 equivalent of triethylamine and 2 equivalents of trifluoroacetic acid.

The acid which can be used in this step may also be used in the form of a dilution with an appropriate solvent in a concentration of 0.1% to 30%. The solvent is not particularly limited as far as it is inert to the reaction, and includes, for example, dichloromethane, acetonitrile, an alcohol(s) (ethanol, isopropanol, trifluoroethanol, etc.), water, or a mixture thereof.

The reaction temperature in the reaction described above is preferably in a range of, e.g., 10° C. to 50° C., more preferably, in a range of 20° C. to 40° C., and most preferably, in a range of 25° C. to 35° C.

The reaction time may vary depending upon kind of the acid used and reaction temperature, and is appropriately in a range of 0.1 minute to 24 hours in general, and preferably in a range of 1 minute to 5 hours.

After completion of this step, a base may be added, if necessary, to neutralize the acid remained in the system. The "base" is not particularly limited and includes, for example, diisopropylethylamine. The base may also be used in the form of a dilution with an appropriate solvent in a concentration of 0.1% (v/v) to 30% (v/v).

The solvent used in this step is not particularly limited so long as it is inert to the reaction, and includes dichloromethane, acetonitrile, an alcohol(s) (ethanol, isopropanol, trifluoroethanol, etc.), water, and a mixture thereof. The reaction temperature is preferably in a range of, e.g., 10° C. to 50° C., more preferably, in a range of 20° C. to 40° C., and most preferably, in a range of 25° C. to 35° C.

The reaction time may vary depending upon kind of the base used and reaction temperature, and is appropriately in a range of 0.1 minute to 24 hours in general, and preferably in a range of 1 minute to 5 hours.

In Compound (II), the compound of general formula (IIa) below (hereinafter Compound (IIa)), wherein n is 1 and L is a group (IV), can be produced by the following procedure.

[Formula 9]

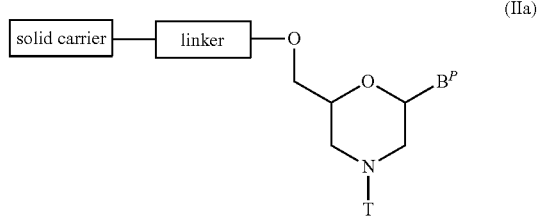
(IIa)

wherein $B^P$, T, linker and solid carrier have the same meaning as defined above.

Step 1:

The compound represented by general formula (V) below is reacted with an acylating agent to prepare the compound represented by general formula (VI) below (hereinafter referred to as Compound (VI)).

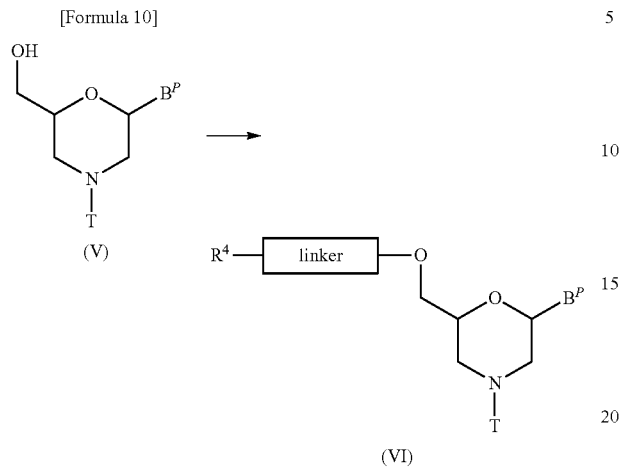

(VI)

wherein $B^P$, T and linker have the same meaning as defined above; and,
$R^4$ represents hydroxy, a halogen, carboxyl group or amino.

This step can be carried out by known procedures for introducing linkers, using Compound (V) as the starting material.

In particular, the compound represented by general formula (VIa) below can be produced by performing the method known as esterification, using Compound (V) and succinic anhydride.

[Formula 11]

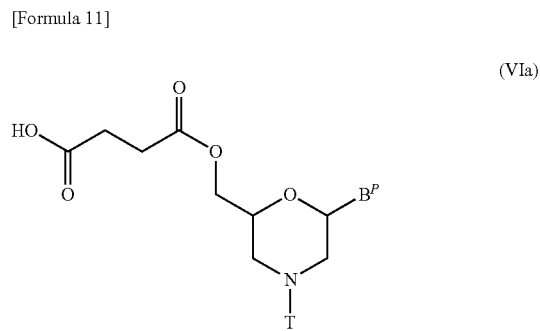

(VIa)

wherein $B^P$ and T have the same meaning as defined above.

Step 2:

Compound (VI) is reacted with a solid career by using a condensing agent or the like to prepare Compound (IIa).

[Formula 12]

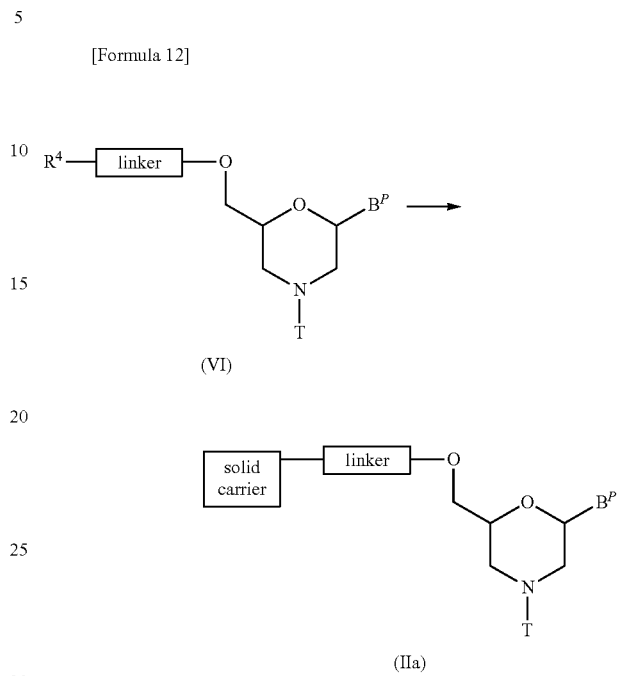

(IIa)

wherein $B^P$, $R^4$, T, linker and solid carrier have the same meaning as defined above.

This step can be performed using Compound (VI) and a solid carrier in accordance with a process known as condensation reaction.

In Compound (II), the compound represented by general formula (IIa2) below wherein n is 1 to 99 (in a specific embodiment, n is, for example, 2 to 29, 2 to 28, 2 to 27, 2 to 26, 2 to 25, 2 to 24, 2 to 23, 2 to 22, 2 to 21 or 2 to 20, preferably a given integer of 19 to 29, 19 to 28, 21 to 29, 21 to 28 or 24 to 28, more preferably 21 to 29, 21 to 28 or 24 to 28) and L is a group represented by general formula (IV) can be produced by using Compound (IIa) as the starting material and repeating step A and step B of the PMO production method described in the specification for a desired number of times.

[Formula 13]

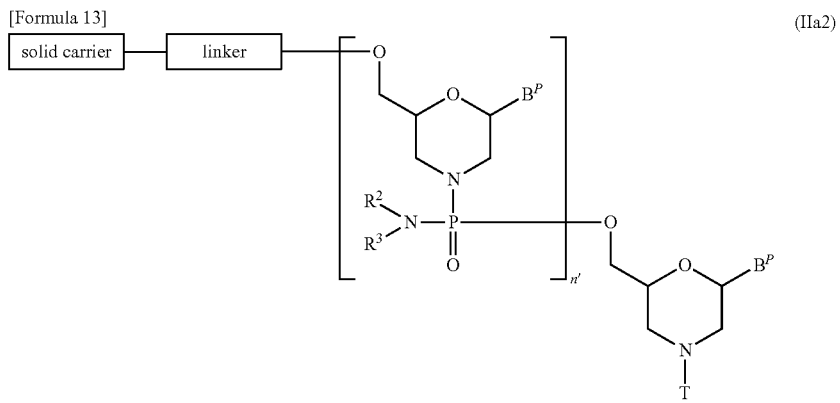

(IIa2)

wherein $B^P$, n, $R^2$, $R^3$, T, linker and solid carrier have the same meaning as defined above.

(2) Step B

Compound (III) is reacted with a morpholino monomer compound in the presence of a base to prepare the compound represented by general formula (VII) below (hereinafter referred to as Compound (VII)):

[Formula 14]

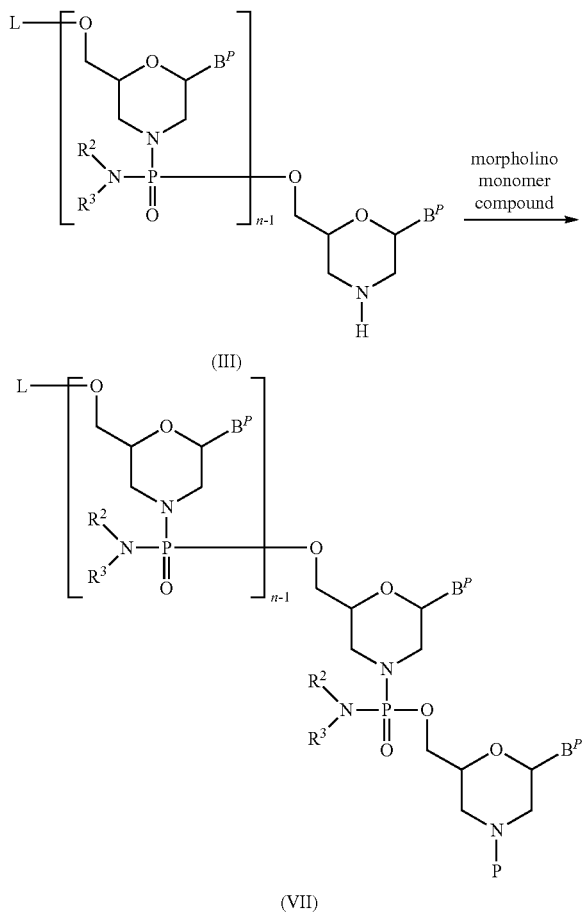

(VII)

wherein each $B^P$, L, n, $R^2$, $R^3$ and T have the same meaning as defined above.

This step can be performed by reacting Compound (III) with the morpholino monomer compound in the presence of a base.

The morpholino monomer compound includes, for example, compounds represented by general formula (VIII) below:

[Formula 15]

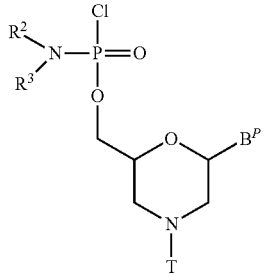

(VIII)

wherein $B^P$, $R^2$, $R^3$ and T have the same meaning as defined above.

The "base" which can be used in this step includes, for example, diisopropylethylamine, triethylamine, and N-ethylmorpholine. The amount of the base used is appropriately, for example, in a range of 1 mol equivalent to 1000 mol equivalents for 1 mol of Compound (III), preferably, 10 mol equivalents to 100 mol equivalents for 1 mol of Compound (III).

The morpholino monomer compound and base which can be used in this step may also be used as a dilution with an appropriate solvent in a concentration of 0.1% to 30%. The solvent is not particularly limited as far as it is inert to the reaction, and includes, for example, N,N-dimethylimidazolidone, N-methylpiperidone, DMF, dichloromethane, acetonitrile, tetrahydrofuran, or a mixture thereof.

The reaction temperature is preferably in a range of, e.g., 0° C. to 100° C., and more preferably, in a range of 10° C. to 50° C.

The reaction time may vary depending upon kind of the base used and reaction temperature, and is appropriately in a range of 1 minute to 48 hours in general, and preferably in a range of 30 minutes to 24 hours.

Furthermore, after completion of this step, an acylating agent can be added, if necessary. The "acylating agent" includes, for example, acetic anhydride, acetyl chloride, and phenoxyacetic anhydride. The acylating agent may also be used as, for example, a dilution with an appropriate solvent in a concentration of 0.1% to 30%. The solvent is not particularly limited as far as it is inert to the reaction, and includes, for example, dichloromethane, acetonitrile, tetrahydrofuran, an alcohol(s) (ethanol, isopropanol, trifluoroethanol, etc.), water, or a mixture thereof.

If necessary, a base such as pyridine, lutidine, collidine, triethylamine, diisopropylethylamine, N-ethylmorpholine, etc. may also be used in combination with the acylating agent. The amount of the acylating agent used is preferably in a range of 0.1 mol equivalent to 10000 mol equivalents, and more preferably in a range of 1 mol equivalent to 1000 mol equivalents. The amount of the base used is appropriately in a range of, e.g., 0.1 mol equivalent to 100 mol equivalents, and preferably in a range of 1 mol equivalent to 10 mol equivalents, for 1 mol of the acylating agent.

The reaction temperature in this reaction is preferably in a range of 10° C. to 50° C., more preferably, in a range of 10° C. to 50° C., much more preferably, in a range of 20° C. to 40° C., and most preferably, in a range of 25° C. to 35° C. The reaction time may vary depending upon kind of the acylating agent used and reaction temperature, and is appropriately in a range of 0.1 minute to 24 hours in general, and preferably in a range of 1 minute to 5 hours.

(3) Step C:

In Compound (VII) produced in Step B, the protective group is removed using a deprotecting agent to prepare the compound represented by general formula (IX).

[Formula 16]

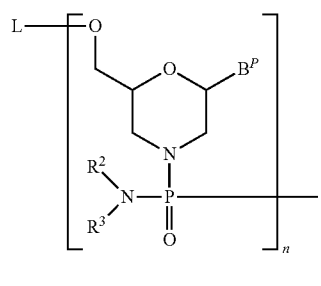

(VII)

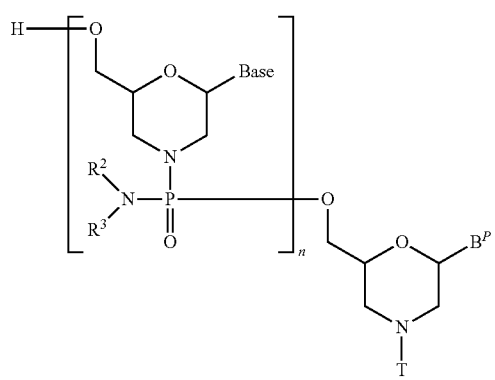

(IX)

wherein Base, $B^P$, L, n, $R^2$, $R^3$ and T have the same meaning as defined above.

This step can be performed by reacting Compound (VII) with a deprotecting agent.

The "deprotecting agent" includes, e.g., conc. ammonia water and methylamine. The "deprotecting agent" used in this step may also be used as a dilution with, e.g., water, methanol, ethanol, isopropyl alcohol, acetonitrile, tetrahydrofuran, DMF, N,N-dimethylimidazolidone, N-methylpiperidone, or a mixture of these solvents. Among them, ethanol is preferred. The amount of the deprotecting agent used is appropriately, for example, in a range of 1 mol equivalent to 100000 mol equivalents, and preferably in a range of 10 mol equivalents to 1000 mol equivalents, for 1 mol of Compound (VII).

The reaction temperature is appropriately, for example, in a range of 15° C. to 75° C., preferably, in a range of 40° C. to 70° C., and more preferably, in a range of 50° C. to 60° C. The reaction time for deprotection may vary depending upon kind of Compound (VII), reaction temperature, etc., and is appropriately in a range of 10 minutes to 30 hours, preferably 30 minutes to 24 hours, and more preferably in a range of 5 hours to 20 hours.

(4) Step D:

PMO (I) is produced by reacting Compound (IX) produced in step C with an acid:

[Formula 17]

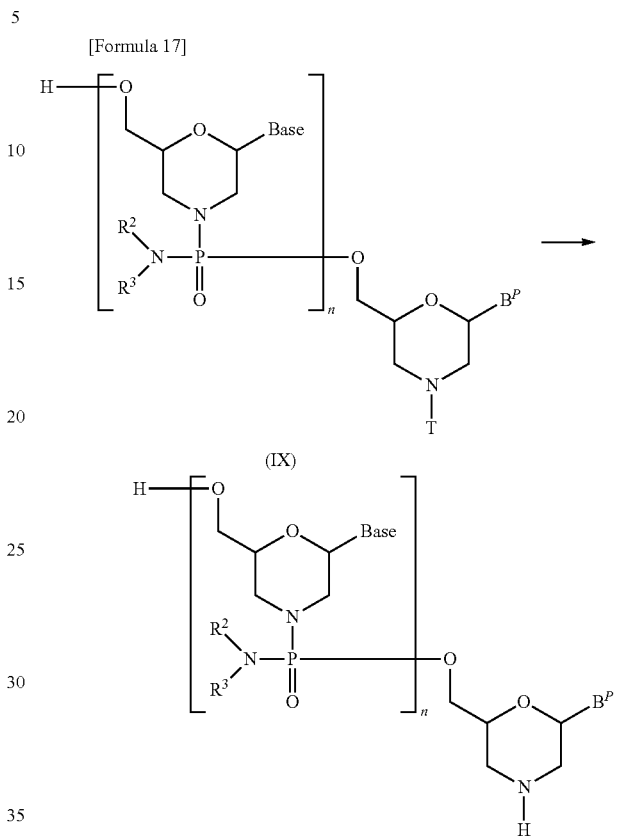

wherein Base, n, $R^2$, $R^3$ and T have the same meaning as defined above.

This step can be performed by adding an acid to Compound (IX).

The "acid" which can be used in this step includes, for example, trichloroacetic acid, dichloroacetic acid, acetic acid, phosphoric acid, hydrochloric acid, etc. The amount of acid used is appropriately used to allow the solution to have a pH range of 0.1 to 4.0, for example, and more preferably, in a range of pH 1.0 to 3.0. The solvent is not particularly limited so long as it is inert to the reaction, and includes, for example, acetonitrile, water, or a mixture of these solvents thereof.

The reaction temperature is preferably in a range of 10° C. to 50° C., more preferably, in a range of 20° C. to 40° C., and more preferably, in a range of 25° C. to 35° C. The reaction time for deprotection may vary depending upon kind of Compound (IX), reaction temperature, etc., and is appropriately in a range of 0.1 minute to 5 hours, preferably 1 minute to 1 hour, and more preferably in a range of 1 minute to 30 minutes.

PMO (I) can be obtained by subjecting the reaction mixture obtained in this step to conventional means of separation and purification such as extraction, concentration, neutralization, filtration, centrifugal separation, recrystallization, reversed phase column chromatography using $C_8$ to $C_{18}$, cation exchange column chromatography, anion exchange column chromatography, gel filtration column chromatography, high performance liquid chromatography, dialysis, ultrafiltration, etc., alone or in combination thereof. Thus, the desired PMO (I) can be isolated and purified (cf., e.g., WO 1991/09033).

In purification of PMO (I) using reversed phase chromatography, as an elution solvent, e.g., a solution mixture of 20 mM triethylamine/acetate buffer and acetonitrile can be used.

In purification of PMO (I) using ion exchange chromatography, as an elution solvent, e.g., a solution mixture of 1 M saline solution and 10 mM sodium hydroxide aqueous solution can be used.

A peptide nucleic acid is the antisense oligomer of the present invention having a group represented by the following general formula as the constituent unit:

[Formula 18]

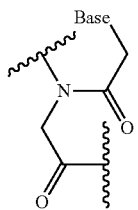

wherein Base has the same meaning as defined above.

Peptide nucleic acids can be prepared by referring to, e.g., the following literatures.

1) P. E. Nielsen, M. Egholm, R. H. Berg, O. Buchardt, Science, 254, 1497 (1991)

2) M. Egholm, O. Buchardt, P. E. Nielsen, R. H. Berg, Jacs., 114, 1895 (1992)

3) K. L. Dueholm, M. Egholm, C. Behrens, L. Christensen, H. F. Hansen, T. Vulpius, K. H. Petersen, R. H. Berg, P. E. Nielsen, O. Buchardt, J. Org. Chem., 59, 5767 (1994)

4) L. Christensen, R. Fitzpatrick, B. Gildea, K. H. Petersen, H. F. Hansen, T. Koch, M. Egholm, O. Buchardt, P. E. Nielsen, J. Coull, R. H. Berg, J. Pept. Sci., 1, 175 (1995)

5) T. Koch, H. F. Hansen, P. Andersen, T. Larsen, H. G. Batz, K. Otteson, H. Orum, J. Pept. Res., 49, 80 (1997)

In the antisense oligomer of the present invention, the 5' end may be any one of the groups shown by the chemical formulae (1) to (3) below, and preferably is (3)-OH.

[Formula 19]

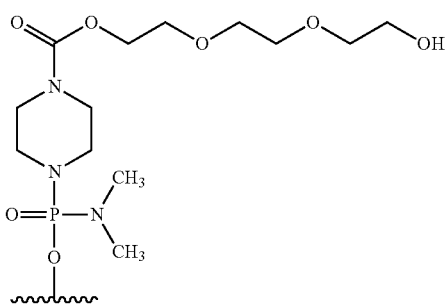

-continued

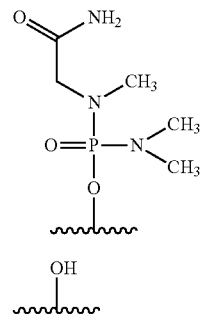

Hereinafter, the groups shown by (1), (2) and (3) above are referred to as "Group (1)," "Group (2)" and "Group (3)," respectively.

The antisense oligomer of the present invention may comprise a compound with a stereochemically optically pure phosphorus atom because the phosphorus atom of the phosphate bond moiety serves as an asymmetric center. A person skilled in the art can obtain pure optically active forms from isomeric mixtures (WO2017/024264). The antisense oligomer of the present invention may be synthesized as a pure optically active form. A person skilled in the art can obtain pure optically active forms by controlling synthesis reactions (JP Laid-Open Publication No. 2018-537952).

2. Peptide Conjugated Antisense Oligomer

The antisense oligomer of the present invention may form a complex with a functional peptide aimed at improving effectiveness (e.g., a membrane-permeable peptide aimed at improving efficacy of delivery to target cells) (WO2008/036127, WO2009/005793, WO2012/150960, WO2016/187425, WO2018/118662, WO2018/118599, WO2018/118627, J. D. Ramsey, N. H. Flynn, Pharmacology & Therapeutics 154, 78-86 (2015), M. K. Tsoumpra et al., EBioMedicine, 45, 630-645(2019)). The conjugation site is not particularly limited. Preferably, the 5' end or 3' end of the antisense oligomer is connected (conjugated) to the amino terminal or carboxyl terminal of the functional peptide.

As another embodiment, the antisense oligomer of the present invention and the functional peptide may form a complex (conjugate) via a linker. The linker is not particularly limited. Preferably, the 5' end or 3' end of the antisense oligomer is connected to one end of the linker while the amino terminal or carboxyl terminal of the functional peptide is connected to the other end of the linker. An additional amino acid may exist between the functional peptide and the linker.

3. Pharmaceutical Composition

The antisense oligomer of the present invention, even if its length is short as compared to the prior art antisense oligomers, can induce exon 51 skipping with high efficiency. The antisense oligomer of the present invention has excellent solubility while maintaining an activity to induce exon 51 skipping with high efficiency. Further, the antisense oligomer of the present invention has excellent solubility and safety while maintaining an activity to induce exon 51 skipping with high efficiency. It is thus expected that conditions of muscular dystrophy can be ameliorated with high efficiency by administering the antisense oligomer of the present invention to DMD patients who have a mutation that is amenable to exon 51 skipping (e.g., frameshift mutation and missense mutation/nonsense mutation in exon 51) in the dystrophin gene. It is thus expected that conditions of muscular dystrophy can be ameliorated with high efficiency by administering the antisense oligomer of the present invention, for example, at least to DMD patients who have predetermined mutant dystrophin gene having deletion of an exon in the vicinity of exon 51. The predetermined mutant dystrophin gene means the dystrophin gene which has at least a frameshift mutation caused by deletion of an exon in the vicinity of exon 51 and in which the amino acid reading frame is corrected by omission (skipping) of exon 51. Examples of the DMD patients include DMD patients with a frameshift mutation caused by deletions of exons 13-50, 29-50, 40-50, 43-50, 45-50, 47-50, 48-50, 49-50, 50, 52, 52-63, etc.

More specifically, it is expected that conditions of muscular dystrophy can be ameliorated with high efficiency by administering the pharmaceutical composition comprising the antisense oligomer of the present invention to DMD patients, who has mutation converting to in-frame by exon 51 skipping, for example, patients with deletion of exon 13-50, patients with deletion of exon 29-50, patients with deletion of exon 40-50, patients with deletion of exon 43-50, patients with deletion of exon 45-50, patients with deletion of exon 47-50, patients with deletion of exon 48-50, patients with deletion of exon 49-50, patients with deletion of exon 50, patients with deletion of exon 52, patients with deletion of exon 52-63, and so on. For example, when the pharmaceutical composition comprising the antisense oligomer of the present invention is used, the same therapeutic effects can be achieved even in a smaller dose than that of the oligomers of the prior art. Accordingly, side effects can be alleviated and such is economical.

The antisense oligomer of the present invention is also useful in preparation of pharmaceutical compositions because the antisense oligomer has excellent solubility while maintaining an activity to induce exon 51 skipping with high efficiency. Further, the antisense oligomer of the present invention is also useful as a pharmaceutical composition because the antisense oligomer has excellent solubility and safety while maintaining an activity to induce exon 51 skipping with high efficiency.

In another embodiment, the present invention provides the pharmaceutical composition for the treatment of muscular dystrophy, comprising as an active ingredient the antisense oligomer of the present invention, a pharmaceutically acceptable salt or hydrate thereof (hereinafter referred to as "the composition of the present invention").

Also, the present invention provides a method for treatment of muscular dystrophy, which comprises administering to a DMD patient the antisense oligomer of the present invention.

In the said method for treatment, the antisense oligomer of the present invention can be administered in the pharmaceutical composition for the treatment of muscular dystrophy.

Furthermore, the present invention provides the use of the antisense oligomer of the present invention in the manufacture of the pharmaceutical composition for treating muscular dystrophy and the antisense oligomer of the present invention for use in the treatment of muscular dystrophy.

Examples of the pharmaceutically acceptable salt of the antisense oligomer of the present invention comprised in the composition of the present invention include alkali metal salts such as sodium salt, potassium salt, and lithium salt; alkaline earth metal salts such as calcium salt and magnesium salt; metal salts such as aluminum salt, iron salt, zinc salt, copper salt, nickel salt, cobalt salt, etc.; ammonium salts; organic amine salts such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, tris(hydroxymethyl)aminomethane salt; hydrohalide salts such as hydrofluoric acid salt, hydrochloride salt, hydrobromide salt, and hydroiodide salt; inorganic acid salts such as nitrate salt, perchlorate salt, sulfate salt, phosphate salt, etc.; lower alkane sulfonates such as methanesulfonate salt, trifluoromethanesulfonate salt, and ethanesulfonate salt; arylsulfonate salt such as benzenesulfonate salt and p-toluenesulfonate salt; organic acid salts such as acetate salt, malate salt, fumarate salt, succinate salt, citrate salt, tartrate salt, oxalate salt, maleate salt, etc.; and, amino acid salts such as glycine salt, lysine salt, arginine salt, ornithine salt, glutamic acid salt, and aspartic acid salt. These salts may be produced by known methods. Alternatively, the antisense oligomer of the present invention comprised in the composition of the present invention may be in the form of a hydrate thereof.

Administration route for the composition of the present invention is not particularly limited so long as it is pharmaceutically acceptable route for administration, and can be chosen depending upon method of treatment. In view of easiness in delivery to muscle tissues, preferred are intravenous administration, intraarterial administration, intramuscular administration, subcutaneous administration, oral administration, tissue administration, transdermal administration, etc. Also, dosage forms which are available for the composition of the present invention are not particularly limited, and include, for example, various injections, oral agents, drips, inhalations, ointments, lotions, etc.

In administration of the antisense oligomer of the present invention to patients with muscular dystrophy, the composition of the present invention may comprise a carrier to promote delivery of the oligomer to muscle tissues. Such a carrier is not particularly limited as far as it is pharmaceutically acceptable, and examples include cationic carriers such as cationic liposomes, cationic polymers, etc., or carriers using viral envelope. Examples of the cationic liposomes include, for example, liposomes composed of 2-O-(2-diethylaminoethy)carabamoyl-1,3-O-dioleoylglycerol and phospholipids as the essential constituents (hereinafter referred to as "liposome A"), Oligofectamine (registered trademark) (Invitrogen Corp.), Lipofectin (registered trademark) (Invitrogen Corp.), Lipofectamine (registered trademark) (Invitrogen Corp.), Lipofectamine 2000 (registered trademark) (Invitrogen Corp.), DMRIE-C (registered trademark) (Invitrogen Corp.), GeneSilencer (registered trademark) (Gene Therapy Systems), TransMessenger (registered trademark) (QIAGEN, Inc.), TransIT TKO (registered trademark) (Minis), and Nucleofector II (Lonza). Among others, liposome A is preferred. Examples of cationic polymers include JetSI (registered trademark) (Qbiogene, Inc.) and Jet-PEI (registered trademark) (polyethylenimine, Qbiogene, Inc.). An example of carriers using viral envelop includes GenomeOne (registered trademark) (HVJ-E liposome, Ishihara Sangyo). Alternatively, the medical devices described in Japanese Patent No. 2924179 and the cationic carriers described in Japanese Domestic Re-Publication PCT Nos. 2006/129594 and 2008/096690 may be used as well.

For further details, U.S. Pat. Nos. 4,235,871, 4,737,323, WO96/14057, "New RRC, Liposomes: A practical approach, IRL Press, Oxford (1990) pages 33-104", etc. can be referred.

A concentration of the antisense oligomer of the present invention comprised in the composition of the present invention may vary depending on kind of the carrier, etc., and in one embodiment, is appropriately in a range of 0.1 nM to 100 μM, preferably in a range of 100 nM to 10 μM. A weight ratio of the antisense oligomer of the present invention comprised in the composition of the present invention and the carrier (carrier/antisense oligomer of the present invention) may vary depending on property of the oligomer, type of the carrier, etc., and is appropriately in a range of 0.1 to 100, preferably in a range of 0.1 to 10.

The composition of the present invention may be in the form of an aqueous solution. In this case, the composition of the present invention may comprise the antisense oligomer of the present invention in a concentration of 2.5 to 500 mg/mL, 5 to 450 mg/mL, 10 to 400 mg/mL, 15 to 350 mg/mL, 20 to 300 mg/mL, 20 to 250 mg/mL, 20 to 200 mg/mL, 20 to 150 mg/mL, 20 to 100 mg/mL, 20 to 50 mg/mL, 20 to 40 mg/mL, 20 to 30 mg/mL, 23 to 27 mg/mL, 24 to 26 mg/mL, or 25 mg/mL. Alternatively, the composition of the present invention may comprise the antisense oligomer of the present invention in a concentration of 10 to 100 mg/mL, 15 to 95 mg/mL, 20 to 80 mg/mL, 25 to 75 mg/mL, 30 to 70 mg/mL, 35 to 65 mg/mL, 40 to 60 mg/mL, 45 to 55 mg/mL, 47 to 53 mg/mL, 48 to 52 mg/mL, 49 to 51 mg/mL, or 50 mg/mL.

The composition of the present invention may be in a dry form. In this case, in order to prepare the composition of the present invention in an aqueous solution form, the composition of the present invention in a dry form comprising, for example, 125 mg or 250 mg of the antisense oligomer of the present invention in a dry form may be mixed with 0.5 mL to 100 mL of water (which corresponds to the antisense oligomer of the present invention in a concentration of 1.25 mg/mL to 250 mg/mL or 2.5 mg/mL to 500 mg/mL), preferably with 1 mL to 50 mL of water (which corresponds to the antisense oligomer of the present invention in a concentration of 2.5 mg/mL to 125 mg/mL or 5 mg/mL to 250 mg/mL), more preferably with 5 mL to 10 mL of water (which correspond to the antisense oligomer of the present invention in a concentration of 12.5 mg/mL to 25 mg/mL or 25 mg/mL to 50 mg/mL) and used.

In addition to the antisense oligomer of the present invention and the carrier described above, pharmaceutically acceptable additives may also be optionally formulated in the composition of the present invention. Examples of such additives are emulsification aids (e.g., fatty acids having 6 to 22 carbon atoms and their pharmaceutically acceptable salts, albumin, and dextran), stabilizers (e.g., cholesterol, phosphatidic acid, sucrose, mannitol, sorbitol, and xylitol), isotonizing agents (e.g., sodium chloride, glucose, maltose, lactose, sucrose, trehalose, mannitol, sorbitol, and xylitol), and pH controlling agents (e.g., hydrochloric acid, sulfuric acid, phosphoric acid, acetic acid, sodium hydroxide, potassium hydroxide, and triethanolamine). One or more of these additives can be used. The content of the additive in the composition of the present invention is appropriately 90 wt % or less, preferably 70 wt % or less, and more preferably, 50 wt % or less.

The composition of the present invention can be prepared by adding the antisense oligomer of the present invention to a carrier dispersion and adequately stirring the mixture. Additives may be added at an appropriate step either before or after addition of the antisense oligomer of the present invention. When the composition of the present invention is in the form of an aqueous solution, an aqueous solvent that can be used in adding the antisense oligomer of the present invention is not particularly limited as far as it is pharmaceutically acceptable, and examples of the aqueous solvent include injectable water or injectable distilled water, electrolyte fluid such as physiological saline, etc., and sugar fluid such as glucose fluid, maltose fluid, etc. A person skilled in the art can appropriately choose conditions for pH and temperature for such case.

The composition of the present invention may be prepared into, e.g., a liquid form and its lyophilized preparation. In one embodiment of the composition of the present invention in a dry form, the lyophilized preparation can be prepared by lyophilizing the composition of the present invention in a liquid form in a conventional manner. The lyophilization can be performed, for example, by appropriately sterilizing the composition of the present invention in a liquid form, dispensing an aliquot into a vial container, performing preliminary freezing for 2 hours at conditions of about −40 to −20° C., performing a primary drying at about 0 to 10° C. under reduced pressure, and then performing a secondary drying at about 15 to 25° C. under reduced pressure. In general, the lyophilized preparation of the composition of the present invention can be then obtained by replacing the gas of the vial with nitrogen gas and capping.

The lyophilized preparation of the composition of the present invention can be used in general upon reconstitution by adding an optional suitable solution (reconstitution liquid) and redissolving the preparation. Such a reconstitution liquid includes injectable water, physiological saline, and other infusion fluids. A volume of the reconstitution liquid may vary depending on the intended use, etc., is not particularly limited, and is suitably 0.5 to 2-fold greater than the volume prior to lyophilization or no more than 500 mL.

It is desired to control a dose of the composition of the present invention to be administered, by taking the following factors into account: the type and dosage form of the antisense oligomer of the present invention comprised in the composition; patients' conditions including age, body weight, etc.; administration route; and the characteristics and extent of the disease. A daily dose calculated as the amount of the antisense oligomer of the present invention is generally in a range of 0.1 mg to 10 g/human, and preferably 1 mg to 1 g/human. This numerical range may vary occasionally depending on type of the target disease, administration route and target molecule. Therefore, a dose lower than the range may be sufficient in some occasion and conversely, a dose higher than the range may be required occasionally. The composition can be administered from once to several times daily or at intervals from one day to several days.

In another embodiment of the composition of the present invention, there is provided a pharmaceutical composition comprising a vector capable of expressing the oligonucleotide of the present invention and the carrier described above. Such an expression vector may be a vector capable of expressing a plurality of the oligonucleotides of the present invention. The composition may be formulated with pharmaceutically acceptable additives as in the case with the composition of the present invention comprising the antisense oligomer of the present invention. A concentration of the expression vector comprised in the composition may vary depending upon type of the career, etc., and in one embodiment, is appropriately in a range of 0.1 nM to 100 μM, preferably in a range of 100 nM to 10 μM. A weight ratio of the expression vector and the carrier comprised in the composition (carrier/expression vector) may vary depending on property of the expression vector, type of the carrier, etc., and is appropriately in a range of 0.1 to 100, preferably in a range of 0.1 to 10. The content of the carrier comprised in the composition is the same as in the case with the composition of the present invention comprising the antisense oligomer of the present invention, and a method for producing the same is also the same as in the case with the composition of the present invention.

Hereinafter, the present invention will be described in more detail with reference to Examples and Test Examples below, but is not deemed to be limited thereto.

EXAMPLES

Example 1: Synthesis of Antisense Oligomer

According to the method described in WO2015/137409, the antisense oligomers shown in Table 1 (PMO Nos. 1 to 93 (SEQ ID NOs: 1 to 93)) which targeted a partial base sequence of exon 51 and/or its 5' adjacent intron (intron 50) in the human dystrophin gene were synthesized. The theoretical value of the molecular weight of each antisense oligomer and the found value thereof by ESI-TOF-MS are also shown in the table.

In Table 1, for example, "H51_67-81_131-142" represents that when the 5'-terminal base of exon 51 in the human dystrophin gene is counted as the 1st base and its downstream bases to the 3' direction are numbered in order, the antisense oligomer targets the sequence of the 67th to 81st bases and the sequence of the 131st to 142nd base. The sequence of the -1st base and its upstream bases in the target base sequence is a base sequence in intron 50. A base sequence including exon 51 and a sequence in the vicinity of 3' end of intron 50 in the human wild-type dystrophin gene is represented by SEQ ID NO: 128.

TABLE 3

Table 1 Synthesized antisense oligomers (PMO No. 1 to 93)

| PMO No. | Target base sequence | Full length | Base sequence of PMO | Molecular weight Theoretical value | Molecular weight Found value | SEQ ID NO |
|---|---|---|---|---|---|---|
| 1 | H51_67-81_131-142 | 27 | TCGGTAAGTTCTAAGATGGCATTTCTA | 8977.10 | 8977.68 | 1 |
| 2 | H51_68-81_131-142 | 26 | TCGGTAAGTTCTAAGATGGCATTTCT | 8637.98 | 8637.42 | 2 |
| 3 | H51_74-89_132-142 | 27 | TCGGTAAGTTCCATCAAGGAAGATGGC | 9021.13 | 9021.40 | 3 |
| 4 | H51_73-89_132-141 | 27 | CGGTAAGTTCCATCAAGGAAGATGGCA | 9030.14 | 9030.55 | 4 |
| 5 | H51_69-81_128-142 | 28 | TCGGTAAGTTCTGTCAAGATGGCATTTC | 9308.21 | 9308.75 | 5 |
| 6 | H51_66-79_131-142 | 26 | TCGGTAAGTTCTGATGGCATTTCTAG | 8653.98 | 8653.47 | 6 |
| 7 | H51_67-79_134-146 | 26 | CCAGTCGGTAAGTGATGGCATTTCTA | 8647.99 | 8647.86 | 7 |
| 8 | H51_68-80_130-142 | 26 | TCGGTAAGTTCTGAGATGGCATTTCT | 8653.98 | 8654.05 | 8 |
| 9 | H51_70-81_129-142 | 26 | TCGGTAAGTTCTGTAAGATGGCATTT | 8677.99 | 8677.82 | 9 |
| 10 | H51_70-81_128-141 | 26 | CGGTAAGTTCTGTCAAGATGGCATTT | 8662.99 | 8663.07 | 10 |
| 11 | H51_68-80_131-142 | 25 | TCGGTAAGTTCTAGATGGCATTTCT | 8298.86 | 8298.84 | 11 |
| 12 | H51_67-78_129-142 | 26 | TCGGTAAGTTCTGTATGGCATTTCTA | 8628.97 | 8628.97 | 12 |
| 13 | H51_67-79_130-142 | 26 | TCGGTAAGTTCTGGATGGCATTTCTA | 8653.98 | 8653.04 | 13 |
| 14 | H51_68-79_129-142 | 26 | TCGGTAAGTTCTGTGATGGCATTTCT | 8644.97 | 8644.45 | 14 |
| 15 | H51_68-79_130-142 | 25 | TCGGTAAGTTCTGGATGGCATTTCT | 8314.86 | 8315.29 | 15 |
| 16 | H51_69-80_129-142 | 26 | TCGGTAAGTTCTGTAGATGGCATTTC | 8653.98 | 8653.51 | 16 |
| 17 | H51_70-81_130-142 | 25 | TCGGTAAGTTCTGAAGATGGCATTT | 8347.88 | 8348.16 | 17 |
| 18 | H51_69-80_131-143 | 25 | GTCGGTAAGTTCTAGATGGCATTTC | 8323.87 | 8324.63 | 18 |
| 19 | H51_69-79_131-142 | 23 | TCGGTAAGTTCTGATGGCATTTC | 7629.63 | 7629.47 | 19 |
| 20 | H51_68-80_130-141 | 25 | CGGTAAGTTCTGAGATGGCATTTCT | 8323.87 | 8323.29 | 20 |
| 21 | H51_69-80_130-142 | 25 | TCGGTAAGTTCTGAGATGGCATTTC | 8323.87 | 8323.51 | 21 |
| 22 | H51_72-82_130-142 | 24 | TCGGTAAGTTCTGGAAGATGGCAT | 8042.78 | 8042.42 | 22 |
| 23 | H51_69-80_129-141 | 25 | CGGTAAGTTCTGTAGATGGCATTTC | 8323.87 | 8324.17 | 23 |
| 24 | H51_70-80_130-141 | 23 | CGGTAAGTTCTGAGATGGCATTT | 7678.65 | 7678.31 | 24 |
| 25 | H51_69-79_130-141 | 23 | CGGTAAGTTCTGGATGGCATTTC | 7654.64 | 7654.67 | 25 |
| 26 | H51_68-78_130-141 | 23 | CGGTAAGTTCTGATGGCATTTCT | 7629.63 | 7629.34 | 26 |

TABLE 3-continued

Table 1 Synthesized antisense oligomers (PMO No. 1 to 93)

| PMO No. | Target base sequence | Full length | Base sequence of PMO | Molecular weight Theoretical value | Molecular weight Found value | SEQ ID NO |
|---|---|---|---|---|---|---|
| 27 | H51_68-78_129-141 | 24 | CGGTAAGTTCTGTATGGCATTTCT | 7959.74 | 7959.98 | 27 |
| 28 | H51_69-79_131-141 | 22 | CGGTAAGTTCTGATGGCATTTC | 7299.52 | 7299.75 | 28 |
| 29 | H51_68-78_132-145 | 25 | CAGTCGGTAAGTTCATGGCATTTCT | 8283.86 | 8283.22 | 29 |
| 30 | H51_73-82_127-141 | 25 | CGGTAAGTTCTGTCCGAAGATGGCA | 8342.89 | 8342.97 | 30 |
| 31 | H51_68-79_129-141 | 25 | CGGTAAGTTCTGTGATGGCATTTCT | 8314.86 | 8314.76 | 31 |
| 32 | H51_68-78_128-141 | 25 | CGGTAAGTTCTGTCATGGCATTTCT | 8274.85 | 8274.92 | 32 |
| 33 | H51_77-89_132-145 | 27 | CAGTCGGTAAGTTCCATCAAGGAAGAT | 9005.13 | 9005.19 | 33 |
| 34 | H51_74-88_131-142 | 27 | TCGGTAAGTTCTATCAAGGAAGATGGC | 9036.13 | 9035.95 | 34 |
| 35 | H51_69-82_133-145 | 27 | CAGTCGGTAAGTTGAAGATGGCATTTC | 9027.12 | 9026.95 | 35 |
| 36 | H51_77-90_137-150 | 28 | AAAGCCAGTCGGTAACATCAAGGAAGAT | 9362.27 | 9362.13 | 36 |
| 37 | H51_74-88_131-145 | 30 | CAGTCGGTAAGTTCTATCAAGGAAGATGGC | 10045.48 | 10045.48 | 37 |
| 38 | H51_77-91_134-148 | 30 | AGCCAGTCGGTAAGTAACATCAAGGAAGAT | 10047.50 | 10047.18 | 38 |
| 39 | H51_77-91_139-150 | 27 | AAAGCCAGTCGGAACATCAAGGAAGAT | 9032.16 | 9032.47 | 39 |
| 40 | H51_69-82_132-145 | 28 | CAGTCGGTAAGTTCGAAGATGGCATTTC | 9342.23 | 9342.41 | 40 |
| 41 | H51_77-89_137-150 | 27 | AAAGCCAGTCGGTACATCAAGGAAGAT | 9023.15 | 9023.88 | 41 |
| 42 | H51_70-81_128-142 | 27 | TCGGTAAGTTCTGTCAAGATGGCATTT | 8993.10 | 8993.92 | 42 |
| 43 | H51_68-81_134-146 | 27 | CCAGTCGGTAAGTAAGATGGCATTTCT | 8987.11 | 8987.53 | 43 |
| 44 | H51_77-88_128-142 | 27 | TCGGTAAGTTCTGTCATCAAGGAAGAT | 9011.12 | 9011.04 | 44 |
| 45 | H51_72-86_131-142 | 27 | TCGGTAAGTTCTCAAGGAAGATGGCAT | 9036.13 | 9036.50 | 45 |
| 46 | H51_73-87_131-143 | 28 | GTCGGTAAGTTCTTCAAGGAAGATGGCA | 9391.25 | 9391.64 | 46 |
| 47 | H51_73-88_131-142 | 28 | TCGGTAAGTTCTATCAAGGAAGATGGCA | 9375.25 | 9375.16 | 47 |
| 48 | H51_78-90_132-145 | 27 | CAGTCGGTAAGTTCACATCAAGGAAGA | 9014.14 | 9014.43 | 48 |
| 49 | H51_77-92_131-141 | 27 | CGGTAAGTTCTCAACATCAAGGAAGAT | 8989.13 | 8988.67 | 49 |
| 50 | H51_77-89_131-143 | 26 | GTCGGTAAGTTCTCATCAAGGAAGAT | 8681.01 | 8680.23 | 50 |
| 51 | H51_77-91_135-146 | 27 | CCAGTCGGTAAGAACATCAAGGAAGAT | 9023.15 | 9022.73 | 51 |
| 52 | H51_77-91_137-149 | 28 | AAGCCAGTCGGTAAACATCAAGGAAGAT | 9362.27 | 9362.60 | 52 |
| 53 | H51_76-89_130-142 | 27 | TCGGTAAGTTCTGCATCAAGGAAGATG | 9036.13 | 9036.49 | 53 |
| 54 | H51_71-85_131-142 | 27 | TCGGTAAGTTCTAAGGAAGATGGCATT | 9051.13 | 9051.24 | 54 |
| 55 | H51_71-87_131-142 | 29 | TCGGTAAGTTCTTCAAGGAAGATGGCATT | 9696.35 | 9696.96 | 55 |
| 56 | H51_74-89_141-152 | 28 | AGAAAGCCAGTCCATCAAGGAAGATGGC | 9363.26 | 9363.78 | 56 |
| 57 | H51_77-91_132-144 | 28 | AGTCGGTAAGTTCAACATCAAGGAAGAT | 9368.26 | 9368.63 | 57 |
| 58 | H51_77-91_133-146 | 29 | CCAGTCGGTAAGTTAACATCAAGGAAGAT | 9683.37 | 9683.05 | 58 |
| 59 | H51_77-91_131-144 | 29 | AGTCGGTAAGTTCTAACATCAAGGAAGAT | 9698.37 | 9698.22 | 59 |
| 60 | H51_77-91_134-146 | 28 | CCAGTCGGTAAGTAACATCAAGGAAGAT | 9353.26 | 9353.46 | 60 |
| 61 | H51_74-89_131-142 | 28 | TCGGTAAGTTCTCATCAAGGAAGATGGC | 9351.24 | 9351.27 | 61 |
| 62 | H51_77-91_136-148 | 28 | AGCCAGTCGGTAAAACATCAAGGAAGAT | 9362.27 | 9362.95 | 62 |
| 63 | H51_-2-12_127-142 | 30 | TCGGTAAGTTCTGTCCTCTGAGTAGGAGCT | 9994.43 | 9995.15 | 63 |

TABLE 3-continued

Table 1 Synthesized antisense oligomers (PMO No. 1 to 93)

| PMO No. | Target base sequence | Full length | Base sequence of PMO | Molecular weight Theoretical value | Molecular weight Found value | SEQ ID NO |
|---|---|---|---|---|---|---|
| 64 | H51_128-141_6-18 | 27 | TAACAGTCTGAGTCGGTAAGTTCTGTC | 8978.10 | 8978.67 | 64 |
| 65 | H51_8-20_128-141 | 27 | CGGTAAGTTCTGTCAGTAACAGTCTGA | 8987.11 | 8987.52 | 65 |
| 66 | H51_4-16_128-141 | 27 | CGGTAAGTTCTGTCACAGTCTGAGTAG | 9003.11 | 9003.22 | 66 |
| 67 | H51_6-17_127-141 | 27 | CGGTAAGTTCTGTCCAACAGTCTGAGT | 8963.09 | 8963.28 | 67 |
| 68 | H51_5-15_128-142 | 26 | TCGGTAAGTTCTGTCCAGTCTGAGTA | 8638.98 | 8638.76 | 68 |
| 69 | H51_5-16_129-142 | 26 | TCGGTAAGTTCTGTACAGTCTGAGTA | 8663.99 | 8633.39 | 69 |
| 70 | H51_6-16_128-142 | 26 | TCGGTAAGTTCTGTCACAGTCTGAGT | 8638.98 | 8638.34 | 70 |
| 71 | H51_5-17_129-142 | 27 | TCGGTAAGTTCTGTAACAGTCTGAGTA | 9002.11 | 9002.21 | 71 |
| 72 | H51_6-17_128-142 | 27 | TCGGTAAGTTCTGTCAACAGTCTGAGT | 8978.10 | 8978.75 | 72 |
| 73 | H51_6-18_129-142 | 27 | TCGGTAAGTTCTGTTAACAGTCTGAGT | 8993.10 | 8993.63 | 73 |
| 74 | H51_2-12_128-142 | 26 | TCGGTAAGTTCTGTCTCTGAGTAGGA | 8678.99 | 8679.82 | 74 |
| 75 | H51_2-11_128-142 | 25 | TCGGTAAGTTCTGTCCTGAGTAGGA | 8348.74 | 8348.88 | 75 |
| 76 | H51_-1-13_131-142 | 26 | TCGGTAAGTTCTGTCTGAGTAGGAGC | 8704.00 | 8703.95 | 76 |
| 77 | H51_5-15_128-141 | 25 | CGGTAAGTTCTGTCCAGTCTGAGTA | 8308.87 | 8308.76 | 77 |
| 78 | H51_4-13_131-142 | 22 | TCGGTAAGTTCTGTCTGAGTAG | 7339.53 | 7339.90 | 78 |
| 79 | H51_-3-7_128-142 | 25 | TCGGTAAGTTCTGTCGTAGGAGCTA | 8348.88 | 8348.60 | 79 |
| 80 | H51_-2-9_129-142 | 25 | TCGGTAAGTTCTGTGAGTAGGAGCT | 8388.89 | 8388.22 | 80 |
| 81 | H51_2-11_127-141 | 25 | CGGTAAGTTCTGTCCCTGAGTAGGA | 8333.88 | 8333.90 | 81 |
| 82 | H51_-2-13_127-138 | 27 | TAAGTTCTGTCCGTCTGAGTAGGAGCT | 8994.10 | 8994.30 | 82 |
| 83 | H51_-7-7_128-141 | 28 | CGGTAAGTTCTGTCGTAGGAGCTAAAAT | 9366.24 | 9366.55 | 83 |
| 84 | H51_-3-11_120-133 | 28 | TCTGTCCAAGCCCGCTGAGTAGGAGCTA | 9288.21 | 9288.36 | 84 |
| 85 | H51_6-18_128-141 | 27 | CGGTAAGTTCTGTCTAACAGTCTGAGT | 8978.10 | 8978.58 | 85 |
| 86 | H51_-1-15_125-136 | 28 | AGTTCTGTCCAACAGTCTGAGTAGGAGC | 9327.22 | 9326.72 | 86 |
| 87 | H51_-1-12_125-138 | 27 | TAAGTTCTGTCCAATCTGAGTAGGAGC | 8987.11 | 8987.28 | 87 |
| 88 | H51_6-17_128-141 | 26 | CGGTAAGTTCTGTCAACAGTCTGAGT | 8647.99 | 8648.53 | 88 |
| 89 | H51_6-18_130-142 | 26 | TCGGTAAGTTCTGTAACAGTCTGAGT | 8662.99 | 8663.19 | 89 |
| 90 | H51_73-87_127-141 | 30 | CGGTAAGTTCTGCCTCAAGGAAGATGGCA | 10021.94 | 10021.47 | 90 |
| 91 | H51_70-82_128-142 | 28 | TCGGTAAGTTCTGTCGAAGATGGCATTT | 9348.22 | 9348.21 | 91 |
| 92 | H51_69-81_128-141 | 27 | CGGTAAGTTCTGTCAAGATGGCATTTC | 8978.10 | 8978.55 | 92 |
| 93 | H51_70-82_127-141 | 28 | CGGTAAGTTCTGTCCGAAGATGGCATTT | 9333.22 | 9333.36 | 93 |

Example 2: Exon Skipping Activity Test of Antisense Oligomer

In Vitro Test of Exon 51 Skipping in Human Dystrophin Gene

1) Testing Method

Using an Amaxa Cell Line Nucleofector Kit L and Nucleofector II (Lonza), 0.3 to 120 µM of each antisense oligomer of Tables 1 and 2 was transfected to $3.5 \times 10^5$ of RD cells (human rhabdomyosarcoma cell line, CCL-136, purchased from ATCC). The pulse program used for the transfection was T-030.

After transfection, the RD cells were cultured for three nights in 2 mL of Eagle's minimal essential medium (EMEM) (Sigma, hereinafter the same) containing 10% fetal bovine serum (FBS) (Invitrogen) under conditions of 37° C. and 5% $CO_2$.

The cultured RD cells were washed once with PBS (Nissui, hereinafter the same) and 350 μL of Buffer RA1 (Takara Bio Inc.) containing 1% 2-mercaptoethanol (Nacalai Tesque, Inc.) was added to the cells. After the cells were allowed to stand at room temperature for a few minutes to lyse the cells, the lysate was collected onto NucleoSpin (registered trademark) Filter (Takara Bio Inc.). A homogenate was produced by centrifugation at 11,000×g for 1 minute. The total RNA was extracted therefrom according to the protocol attached to NucleoSpin (registered trademark) RNA (Takara Bio Inc.). The concentration of the total RNA extracted was determined using a NanoDrop ONE (Thermo Fisher Scientific Inc.).

One-Step RT-PCR was performed with 400 ng of the extracted total RNA using a QIAGEN One Step RT-PCR Kit (Qiagen) and a thermal cycler. A reaction solution was prepared in accordance with the protocol attached to the kit. The thermal cycler used was TaKaRa PCR Thermal Cycler Dice Touch (Takara Bio Inc.). The RT-PCR program used was as follows.

50° C., 30 minutes: reverse transcription reaction
95° C., 15 minutes: polymerase activation, reverse transcriptase inactivation, cDNA thermal denaturation
[94° C., 30 seconds; 60° C., 30 seconds; 72° C., 1 minute]×35 cycles: PCR amplification
72° C., 10 minutes: final extension The base sequences of the forward primer and reverse primer used for RT-PCR are given below.

```
Forward primer:
                                     (SEQ ID NO: 95)
5'-CTGAGTGGAAGGCGGTAAAC-3'

Reverse primer:
                                     (SEQ ID NO: 96)
5'-GAAGTTTCAGGGCCAAGTCA-3'
```

The reaction product, 1 μL of the PCR above was analyzed using a Bioanalyzer (Agilent Technologies, Inc.) or MultiNA (Shimadzu Corp.).

The polynucleotide level of the band showing that exon 51 was skipped (the polynucleotide level "A") and the polynucleotide level of the band showing that exon 51 was not skipped (the polynucleotide level "B") were measured as signal intensities of the bands. Based on these measurement values of "A" and "B", the skipping efficiency was determined by the equation (1) mentioned above.

(2) Test Results

FIGS. 1 to 18 show the results about the exon 51 skipping efficiency obtained as to each antisense oligomer. The antisense oligomer shown in Table 2 (PMO No. 94 (SEQ ID NO: 94)) which had the same base sequence as that of the exon 51 skipping drug eteplirsen (WHO Drug Information 24, 2, 137-139 (2010), Proposed INN List 103) and had the same 5'-terminal modification thereas in which the 5' end had the group (1) described above; thus, was structurally the same as a whole thereas was synthesized according to the method described in Japanese Patent Laid-Open No. 2015-91229 and used as a direct or indirect comparative control.

The antisense oligomers of the present invention shown in Table 1 had significantly higher skipping efficiency than that of the antisense oligomer of Table 2 which was structurally the same as a whole as eteplirsen. The antisense oligomers of the present invention exceedingly effectively skipped exon 51.

TABLE 4

Table 2 Synthesized antisense oligomer (PMO No. 94) having same base sequence and 5'-terminal modification as those of eteplirsen

| PMO No. | Target base sequence | Full length | Base sequence of PMO | Molecular weight Theoretical value | Molecular weight Found value | SEQ ID NO |
|---|---|---|---|---|---|---|
| 94 | H51_66-95 | 30 | CTCCAACATCAAGGAAGATGGCATTTCTAG | 10300.59 | 10300.43 | 94 |

Example 3: Solubility Test of Antisense Oligomer

Solubility Test of Antisense Oligomer in Physiological Saline

Each antisense oligomer of PMO Nos. 7, 8, 10, 16, 21, 24, 31, 42, 67, 76, and 90 with very high skipping efficiency in Example 2 was tested for its solubility in physiological saline in order to further verify usefulness for medical application.

(1) Testing Method

57 μL of injectable water was added to a sample bottle containing 5.7 mg of each antisense oligomer above, which was then dissolved using ultrasonic waves and vortex. Then, 57 μL of 2×physiological saline was added thereto and stirred using vortex to prepare a 50 mg/mL physiological saline solution. The solution was allowed to stand at room temperature for 24 hours, and the presence or absence of precipitation in the solution thus allowed to stand was visually confirmed. An antisense oligomer that caused no precipitation was evaluated as having high solubility.

(2) Test Results

Among the antisense oligomers tested, each antisense oligomer of PMO Nos. 7, 8, 10, 16, 21, 24, 31, 42, 67, and 76 exhibited solubility equal to or higher than 50 mg/mL in physiological saline.

From the results, these antisense oligomers were found to be antisense oligomers highly useful as medicaments because of their significantly high efficiency of exon 51 skipping as well as high solubility in physiological saline.

Example 4: Safety Evaluation of Antisense Oligomer

Among the antisense oligomers tested for their solubility in physiological saline in Example 3, each antisense oligomer of PMO Nos. 16, 21, 42, and 90 was evaluated for its safety in order to verify safety for medical application.

(1) Evaluation Method

Each antisense oligomer was dissolved in physiological saline and administered into the tail vein of a C57BL/6N male 6-week-old mouse. On the next day, serum was collected from the mouse, and its aspartate aminotransferase (AST) value, alanine aminotransferase (ALT) value, blood urea nitrogen (BUN) value and creatinine value in blood were measured. Measurement values of a control group of mice given only physiological saline used as a medium or untreated mice were regarded as normal values, and a statistically significant difference test (Student's t test or Dunnett test) was conducted. When significant elevation was seen in the values with a significance level of $p<0.05$ in the administration group of each antisense oligomer, the values were determined as outliers. In each test, statistical analysis system SAS (registered trademark, SAS Institute Inc.) version 9.3 was used. When no outlier was seen in any of the AST value, the ALT value, the BUN value and the creatinine value at a dose of 1000 mg/kg, the antisense oligomer was determined to have high safety.

(2) Evaluation Results

Figure 19:
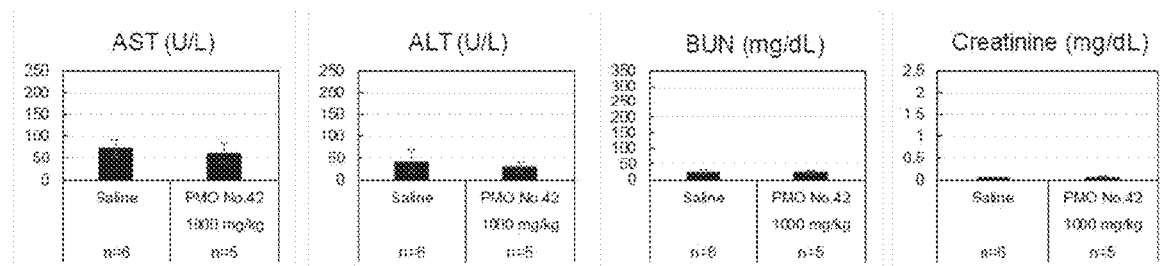
FIG. 19 shows results of a safety test of an antisense oligomer of PMO No. 42 in mice. An aspartate aminotransferase (AST) value, an alanine aminotransferase (ALT) value, a blood urea nitrogen (BUN) value, and a creatinine value are indicated in order from the left by mean±standard deviation (significance level based on the Student's t test: p<0.05).
Figure 20:
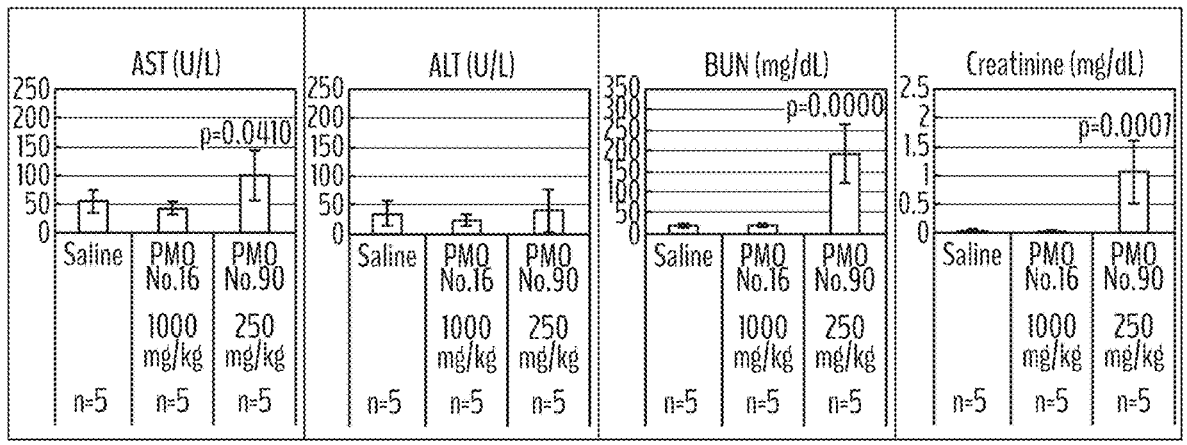
FIG. 20 shows results of a safety test of antisense oligomers of PMO Nos. 16 and 90 in mice. An AST value, an ALT value, a BUN value, and a creatinine value are indicated in order from the left by mean±standard deviation, and a value found to have significant elevation is indicated by p value (significance level based on the Dunnett test: p<0.05).
Figure 21:
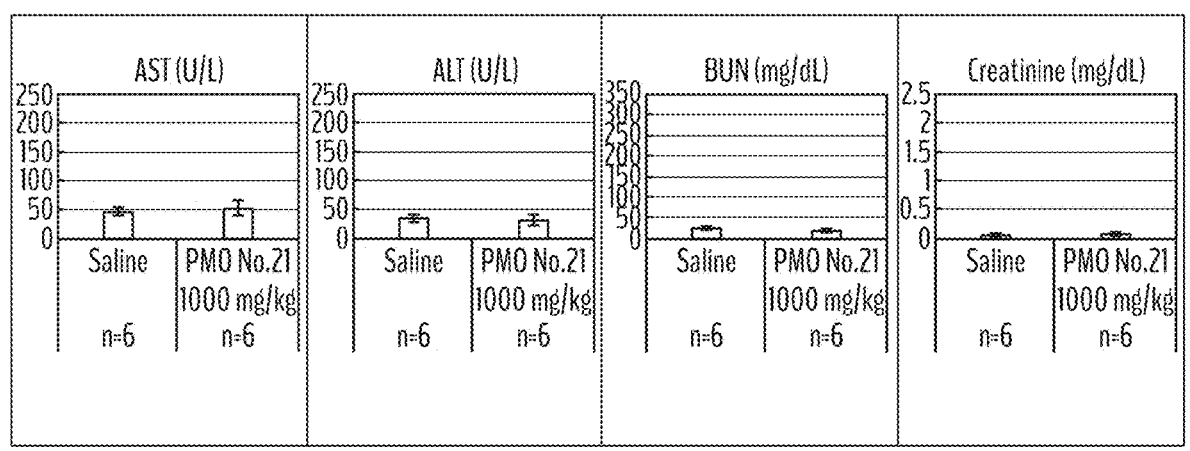
FIG. 21 shows results of a safety test of an antisense oligomer of PMO No. 21 in mice. An AST value, an ALT value, a BUN value, and a creatinine value are indicated in order from the left by mean±standard deviation (significance level based on the Student's t test: p<0.05).

Each antisense oligomer of PMO Nos. 16, 21, and 42 exhibited no outlier in any of the AST value, the ALT value, the BUN value and the creatinine value at a dose of 1000 mg/kg, and was confirmed to have high safety (specifically, to have no influence on or to be very unlikely to have influence on the functions of the kidney and the liver). Their respective results are shown in FIGS. 19 to 21. Values found to have significant elevation with a significance level of $p<0.05$ (outliers) are indicated by p value.

These results demonstrated that the antisense oligomer of the present invention has excellent physical properties and safety as medicaments while exhibiting an activity to induce exon 51 skipping in the dystrophin gene with high efficiency.

Free Text of Sequence Listing

SEQ ID NOs: 1 to 126: synthetic nucleic acids

The invention claimed is:

1. An antisense oligomer consisting of the base sequence of any of SEQ ID NOs: 7, 8, 10, 16, 21, 24, 31, 42, 67, and 76, or a pharmaceutically acceptable salt or hydrate thereof, wherein the antisense oligomer is (i) an oligonucleotide comprising at least one nucleotide having a modified sugar moiety or a modified phosphate bond moiety, or (ii) a morpholino oligomer.

2. The antisense oligomer or the pharmaceutically acceptable salt or hydrate thereof according to claim 1, wherein the antisense oligomer is the oligonucleotide.

3. The antisense oligomer or the pharmaceutically acceptable salt or hydrate thereof according to claim 2, wherein the oligonucleotide comprises at least one nucleotide having a modified sugar moiety, and wherein the modified sugar moiety is a ribose in which the 2'-OH group is replaced by OR, R, R'OR, SH, SR, $NH_2$, NHR, $NR_2$, $N_3$, CN, F, Cl, Br, or I (wherein R is an alkyl or an aryl, and R' is an alkylene).

4. The antisense oligomer or the pharmaceutically acceptable salt or hydrate thereof according to claim 2, wherein the oligonucleotide comprises at least one nucleotide having a modified phosphate bond moiety, and wherein the modified phosphate bond moiety is a phosphorothioate bond, a phosphorodithioate bond, an alkylphosphonate bond, a phosphoramidate bond, or a boranophosphate bond.

5. The antisense oligomer or the pharmaceutically acceptable salt or hydrate thereof according to claim 1, wherein the antisense oligomer is a morpholino oligomer.

6. The antisense oligomer or the pharmaceutically acceptable salt or hydrate thereof according to claim 5, wherein the antisense oligomer is a phosphorodiamidate morpholino oligomer.

7. The antisense oligomer or the pharmaceutically acceptable salt or hydrate thereof according to claim 5, wherein the 5' end is any one of chemical formulae (1) to (3) below:

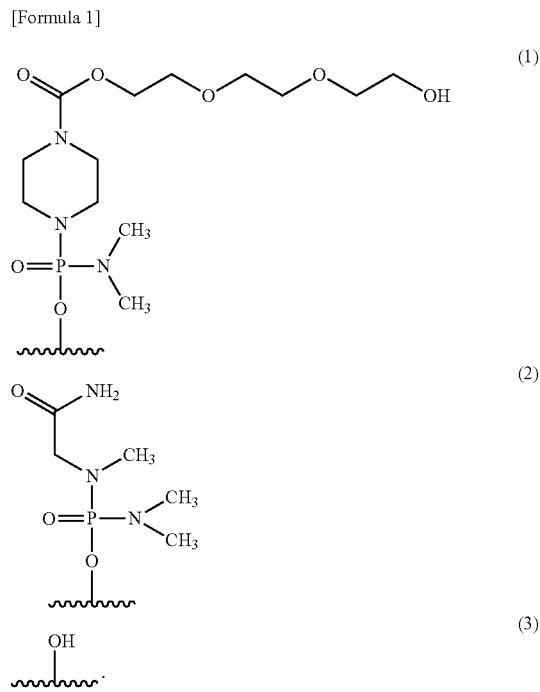

8. A pharmaceutical composition comprising (i) the antisense oligomer or the pharmaceutically acceptable salt or hydrate thereof according to claim 1, and (ii) a pharmaceutically acceptable carrier, a pharmaceutically acceptable additive, or an aqueous solvent.

9. A method for treatment of muscular dystrophy in a patient in need thereof comprising:

administering to the patient an effective amount of
(a) the antisense oligomer or the pharmaceutically acceptable salt or hydrate thereof according to claim 1,
(b) a pharmaceutical composition comprising (i) the antisense oligomer or the pharmaceutically acceptable salt or hydrate thereof according to claim 1, and (ii) a pharmaceutically acceptable carrier, a pharmaceutically acceptable additive, or an aqueous solvent, or
(c) a pharmaceutical composition comprising (i) the antisense oligomer or the pharmaceutically acceptable salt or hydrate thereof according to claim 1, and (ii) a carrier that promotes delivery of the antisense oligomer to muscle tissues.

10. The method for treatment according to claim 9, wherein the patient is a human.

11. The method for treatment according to claim 9, wherein the patient carries a dystrophin gene mutation to be converted to in-frame by exon 51 skipping.

12. The method for treatment according to claim 11, wherein the mutation is a frameshift mutation caused by deletion of an exon in the vicinity of exon 51 of the dystrophin gene.

13. The method for treatment according to claim 12, wherein the frameshift mutation is caused by (i) a deletion of exons 13-50 in the dystrophin gene, (ii) a deletion of exons 29-50 in the dystrophin gene, (iii) a deletion of exons 40-50 in the dystrophin gene, (iv) a deletion of exons 43-50 in the dystrophin gene, (v) a deletion of exons 45-50 in the dystrophin gene, (vi) a deletion of exons 47-50 in the dystrophin gene, (vii) a deletion of exons 48-50 in the dystrophin gene, (viii) a deletion of exons 49-50 in the dystrophin gene, (ix) a deletion of exon 50 in the dystrophin gene, (x) a deletion of exon 52 in the dystrophin gene, or (xi) a deletion of exons 52-63 in the dystrophin gene.

14. The antisense oligomer or the pharmaceutically acceptable salt or hydrate thereof according to claim 1, wherein the antisense oligomer consists of the base sequence of SEQ ID NO: 16, SEQ ID NO: 21, or SEQ ID NO: 42.

15. The antisense oligomer or the pharmaceutically acceptable salt or hydrate thereof according to claim 1, wherein the antisense oligomer consists of the base sequence of SEQ ID NO: 16.

16. The antisense oligomer or the pharmaceutically acceptable salt or hydrate thereof according to claim 1, wherein the antisense oligomer consists of the base sequence of SEQ ID NO: 21.

17. The antisense oligomer or the pharmaceutically acceptable salt or hydrate thereof according to claim 1, wherein the antisense oligomer consists of the base sequence of SEQ ID NO: 42.

18. A pharmaceutical composition comprising (i) the antisense oligomer or the pharmaceutically acceptable salt or hydrate thereof according to claim 1, and (ii) a carrier that promotes delivery of the antisense oligomer to muscle tissues.

19. The pharmaceutical composition according to claim 18, wherein the carrier is a cationic polymer.

* * * * *

```
SEQUENCE LISTING

Sequence total quantity: 128
SEQ ID NO: 1            moltype = DNA  length = 27
FEATURE                 Location/Qualifiers
misc_feature            1..27
                        note = Synthetic Nucleic Acid
source                  1..27
                        mol_type = other DNA
                        organism = synthetic construct
SEQUENCE: 1
tcggtaagtt ctaagatggc atttcta                                              27

SEQ ID NO: 2            moltype = DNA  length = 26
FEATURE                 Location/Qualifiers
misc_feature            1..26
                        note = Synthetic Nucleic Acid
source                  1..26
                        mol_type = other DNA
                        organism = synthetic construct
SEQUENCE: 2
tcggtaagtt ctaagatggc atttct                                               26

SEQ ID NO: 3            moltype = DNA  length = 27
FEATURE                 Location/Qualifiers
misc_feature            1..27
                        note = Synthetic Nucleic Acid
source                  1..27
                        mol_type = other DNA
                        organism = synthetic construct
SEQUENCE: 3
tcggtaagtt ccatcaagga agatggc                                              27

SEQ ID NO: 4            moltype = DNA  length = 27
FEATURE                 Location/Qualifiers
misc_feature            1..27
                        note = Synthetic Nucleic Acid
source                  1..27
                        mol_type = other DNA
                        organism = synthetic construct
SEQUENCE: 4
cggtaagttc catcaaggaa gatggca                                              27

SEQ ID NO: 5            moltype = DNA  length = 28
FEATURE                 Location/Qualifiers
misc_feature            1..28
                        note = Synthetic Nucleic Acid
source                  1..28
                        mol_type = other DNA
                        organism = synthetic construct
SEQUENCE: 5
tcggtaagtt ctgtcaagat ggcatttc                                             28
```

```
SEQ ID NO: 6            moltype = DNA   length = 26
FEATURE                 Location/Qualifiers
misc_feature            1..26
                        note = Synthetic Nucleic Acid
source                  1..26
                        mol_type = other DNA
                        organism = synthetic construct
SEQUENCE: 6
tcggtaagtt ctgatggcat ttctag                                              26

SEQ ID NO: 7            moltype = DNA   length = 26
FEATURE                 Location/Qualifiers
misc_feature            1..26
                        note = Synthetic Nucleic Acid
source                  1..26
                        mol_type = other DNA
                        organism = synthetic construct
SEQUENCE: 7
ccagtcggta agtgatggca tttcta                                              26

SEQ ID NO: 8            moltype = DNA   length = 26
FEATURE                 Location/Qualifiers
misc_feature            1..26
                        note = Synthetic Nucleic Acid
source                  1..26
                        mol_type = other DNA
                        organism = synthetic construct
SEQUENCE: 8
tcggtaagtt ctgagatggc atttct                                              26

SEQ ID NO: 9            moltype = DNA   length = 26
FEATURE                 Location/Qualifiers
misc_feature            1..26
                        note = Synthetic Nucleic Acid
source                  1..26
                        mol_type = other DNA
                        organism = synthetic construct
SEQUENCE: 9
tcggtaagtt ctgtaagatg gcattt                                              26

SEQ ID NO: 10           moltype = DNA   length = 26
FEATURE                 Location/Qualifiers
misc_feature            1..26
                        note = Synthetic Nucleic Acid
source                  1..26
                        mol_type = other DNA
                        organism = synthetic construct
SEQUENCE: 10
cggtaagttc tgtcaagatg gcattt                                              26

SEQ ID NO: 11           moltype = DNA   length = 25
FEATURE                 Location/Qualifiers
misc_feature            1..25
                        note = Synthetic Nucleic Acid
source                  1..25
                        mol_type = other DNA
                        organism = synthetic construct
SEQUENCE: 11
tcggtaagtt ctagatggca tttct                                               25

SEQ ID NO: 12           moltype = DNA   length = 26
FEATURE                 Location/Qualifiers
misc_feature            1..26
                        note = Synthetic Nucleic Acid
source                  1..26
                        mol_type = other DNA
                        organism = synthetic construct
SEQUENCE: 12
tcggtaagtt ctgtatggca tttcta                                              26

SEQ ID NO: 13           moltype = DNA   length = 26
FEATURE                 Location/Qualifiers
misc_feature            1..26
                        note = Synthetic Nucleic Acid
source                  1..26
                        mol_type = other DNA
                        organism = synthetic construct
```

```
SEQUENCE: 13
tcggtaagtt ctggatggca tttcta                                              26

SEQ ID NO: 14         moltype = DNA   length = 26
FEATURE               Location/Qualifiers
misc_feature          1..26
                      note = Synthetic Nucleic Acid
source                1..26
                      mol_type = other DNA
                      organism = synthetic construct
SEQUENCE: 14
tcggtaagtt ctgtgatggc atttct                                              26

SEQ ID NO: 15         moltype = DNA   length = 25
FEATURE               Location/Qualifiers
misc_feature          1..25
                      note = Synthetic Nucleic Acid
source                1..25
                      mol_type = other DNA
                      organism = synthetic construct
SEQUENCE: 15
tcggtaagtt ctggatggca tttct                                               25

SEQ ID NO: 16         moltype = DNA   length = 26
FEATURE               Location/Qualifiers
misc_feature          1..26
                      note = Synthetic Nucleic Acid
source                1..26
                      mol_type = other DNA
                      organism = synthetic construct
SEQUENCE: 16
tcggtaagtt ctgtagatgg catttc                                              26

SEQ ID NO: 17         moltype = DNA   length = 25
FEATURE               Location/Qualifiers
misc_feature          1..25
                      note = Synthetic Nucleic Acid
source                1..25
                      mol_type = other DNA
                      organism = synthetic construct
SEQUENCE: 17
tcggtaagtt ctgaagatgg cattt                                               25

SEQ ID NO: 18         moltype = DNA   length = 25
FEATURE               Location/Qualifiers
misc_feature          1..25
                      note = Synthetic Nucleic Acid
source                1..25
                      mol_type = other DNA
                      organism = synthetic construct
SEQUENCE: 18
gtcggtaagt tctagatggc atttc                                               25

SEQ ID NO: 19         moltype = DNA   length = 23
FEATURE               Location/Qualifiers
misc_feature          1..23
                      note = Synthetic Nucleic Acid
source                1..23
                      mol_type = other DNA
                      organism = synthetic construct
SEQUENCE: 19
tcggtaagtt ctgatggcat ttc                                                 23

SEQ ID NO: 20         moltype = DNA   length = 25
FEATURE               Location/Qualifiers
misc_feature          1..25
                      note = Synthetic Nucleic Acid
source                1..25
                      mol_type = other DNA
                      organism = synthetic construct
SEQUENCE: 20
cggtaagttc tgagatggca tttct                                               25
```

```
SEQ ID NO: 21            moltype = DNA  length = 25
FEATURE                  Location/Qualifiers
misc_feature             1..25
                         note = Synthetic Nucleic Acid
source                   1..25
                         mol_type = other DNA
                         organism = synthetic construct
SEQUENCE: 21
tcggtaagtt ctgagatggc atttc                                          25

SEQ ID NO: 22            moltype = DNA  length = 24
FEATURE                  Location/Qualifiers
misc_feature             1..24
                         note = Synthetic Nucleic Acid
source                   1..24
                         mol_type = other DNA
                         organism = synthetic construct
SEQUENCE: 22
tcggtaagtt ctggaagatg gcat                                           24

SEQ ID NO: 23            moltype = DNA  length = 25
FEATURE                  Location/Qualifiers
misc_feature             1..25
                         note = Synthetic Nucleic Acid
source                   1..25
                         mol_type = other DNA
                         organism = synthetic construct
SEQUENCE: 23
cggtaagttc tgtagatggc atttc                                          25

SEQ ID NO: 24            moltype = DNA  length = 23
FEATURE                  Location/Qualifiers
misc_feature             1..23
                         note = Synthetic Nucleic Acid
source                   1..23
                         mol_type = other DNA
                         organism = synthetic construct
SEQUENCE: 24
cggtaagttc tgagatggca ttt                                            23

SEQ ID NO: 25            moltype = DNA  length = 23
FEATURE                  Location/Qualifiers
misc_feature             1..23
                         note = Synthetic Nucleic Acid
source                   1..23
                         mol_type = other DNA
                         organism = synthetic construct
SEQUENCE: 25
cggtaagttc tggatggcat ttc                                            23

SEQ ID NO: 26            moltype = DNA  length = 23
FEATURE                  Location/Qualifiers
misc_feature             1..23
                         note = Synthetic Nucleic Acid
source                   1..23
                         mol_type = other DNA
                         organism = synthetic construct
SEQUENCE: 26
cggtaagttc tgatggcatt tct                                            23

SEQ ID NO: 27            moltype = DNA  length = 24
FEATURE                  Location/Qualifiers
misc_feature             1..24
                         note = Synthetic Nucleic Acid
source                   1..24
                         mol_type = other DNA
                         organism = synthetic construct
SEQUENCE: 27
cggtaagttc tgtatggcat ttct                                           24

SEQ ID NO: 28            moltype = DNA  length = 22
FEATURE                  Location/Qualifiers
misc_feature             1..22
                         note = Synthetic Nucleic Acid
source                   1..22
                         mol_type = other DNA
                         organism = synthetic construct
```

```
SEQUENCE: 28
cggtaagttc tgatggcatt tc                                          22

SEQ ID NO: 29           moltype = DNA   length = 25
FEATURE                 Location/Qualifiers
misc_feature            1..25
                        note = Synthetic Nucleic Acid
source                  1..25
                        mol_type = other DNA
                        organism = synthetic construct
SEQUENCE: 29
cagtcggtaa gttcatggca tttct                                       25

SEQ ID NO: 30           moltype = DNA   length = 25
FEATURE                 Location/Qualifiers
misc_feature            1..25
                        note = Synthetic Nucleic Acid
source                  1..25
                        mol_type = other DNA
                        organism = synthetic construct
SEQUENCE: 30
cggtaagttc tgtccgaaga tggca                                       25

SEQ ID NO: 31           moltype = DNA   length = 25
FEATURE                 Location/Qualifiers
misc_feature            1..25
                        note = Synthetic Nucleic Acid
source                  1..25
                        mol_type = other DNA
                        organism = synthetic construct
SEQUENCE: 31
cggtaagttc tgtgatggca tttct                                       25

SEQ ID NO: 32           moltype = DNA   length = 25
FEATURE                 Location/Qualifiers
misc_feature            1..25
                        note = Synthetic Nucleic Acid
source                  1..25
                        mol_type = other DNA
                        organism = synthetic construct
SEQUENCE: 32
cggtaagttc tgtcatggca tttct                                       25

SEQ ID NO: 33           moltype = DNA   length = 27
FEATURE                 Location/Qualifiers
misc_feature            1..27
                        note = Synthetic Nucleic Acid
source                  1..27
                        mol_type = other DNA
                        organism = synthetic construct
SEQUENCE: 33
cagtcggtaa gttccatcaa ggaagat                                     27

SEQ ID NO: 34           moltype = DNA   length = 27
FEATURE                 Location/Qualifiers
misc_feature            1..27
                        note = Synthetic Nucleic Acid
source                  1..27
                        mol_type = other DNA
                        organism = synthetic construct
SEQUENCE: 34
tcggtaagtt ctatcaagga agatggc                                     27

SEQ ID NO: 35           moltype = DNA   length = 27
FEATURE                 Location/Qualifiers
misc_feature            1..27
                        note = Synthetic Nucleic Acid
source                  1..27
                        mol_type = other DNA
                        organism = synthetic construct
SEQUENCE: 35
cagtcggtaa gttgaagatg gcatttc                                     27
```

```
SEQ ID NO: 36          moltype = DNA  length = 28
FEATURE                Location/Qualifiers
misc_feature           1..28
                       note = Synthetic Nucleic Acid
source                 1..28
                       mol_type = other DNA
                       organism = synthetic construct
SEQUENCE: 36
aaagccagtc ggtaacatca aggaagat                                            28

SEQ ID NO: 37          moltype = DNA  length = 30
FEATURE                Location/Qualifiers
misc_feature           1..30
                       note = Synthetic Nucleic Acid
source                 1..30
                       mol_type = other DNA
                       organism = synthetic construct
SEQUENCE: 37
cagtcggtaa gttctatcaa ggaagatggc                                          30

SEQ ID NO: 38          moltype = DNA  length = 30
FEATURE                Location/Qualifiers
misc_feature           1..30
                       note = Synthetic Nucleic Acid
source                 1..30
                       mol_type = other DNA
                       organism = synthetic construct
SEQUENCE: 38
agccagtcgg taagtaacat caaggaagat                                          30

SEQ ID NO: 39          moltype = DNA  length = 27
FEATURE                Location/Qualifiers
misc_feature           1..27
                       note = Synthetic Nucleic Acid
source                 1..27
                       mol_type = other DNA
                       organism = synthetic construct
SEQUENCE: 39
aaagccagtc ggaacatcaa ggaagat                                             27

SEQ ID NO: 40          moltype = DNA  length = 28
FEATURE                Location/Qualifiers
misc_feature           1..28
                       note = Synthetic Nucleic Acid
source                 1..28
                       mol_type = other DNA
                       organism = synthetic construct
SEQUENCE: 40
cagtcggtaa gttcgaagat ggcatttc                                            28

SEQ ID NO: 41          moltype = DNA  length = 27
FEATURE                Location/Qualifiers
misc_feature           1..27
                       note = Synthetic Nucleic Acid
source                 1..27
                       mol_type = other DNA
                       organism = synthetic construct
SEQUENCE: 41
aaagccagtc ggtacatcaa ggaagat                                             27

SEQ ID NO: 42          moltype = DNA  length = 27
FEATURE                Location/Qualifiers
misc_feature           1..27
                       note = Synthetic Nucleic Acid
source                 1..27
                       mol_type = other DNA
                       organism = synthetic construct
SEQUENCE: 42
tcggtaagtt ctgtcaagat ggcattt                                             27

SEQ ID NO: 43          moltype = DNA  length = 27
FEATURE                Location/Qualifiers
misc_feature           1..27
                       note = Synthetic Nucleic Acid
source                 1..27
                       mol_type = other DNA
                       organism = synthetic construct
```

```
SEQUENCE: 43
ccagtcggta agtaagatgg catttct                                              27

SEQ ID NO: 44          moltype = DNA   length = 27
FEATURE                Location/Qualifiers
misc_feature           1..27
                       note = Synthetic Nucleic Acid
source                 1..27
                       mol_type = other DNA
                       organism = synthetic construct
SEQUENCE: 44
tcggtaagtt ctgtcatcaa ggaagat                                              27

SEQ ID NO: 45          moltype = DNA   length = 27
FEATURE                Location/Qualifiers
misc_feature           1..27
                       note = Synthetic Nucleic Acid
source                 1..27
                       mol_type = other DNA
                       organism = synthetic construct
SEQUENCE: 45
tcggtaagtt ctcaaggaag atggcat                                              27

SEQ ID NO: 46          moltype = DNA   length = 28
FEATURE                Location/Qualifiers
misc_feature           1..28
                       note = Synthetic Nucleic Acid
source                 1..28
                       mol_type = other DNA
                       organism = synthetic construct
SEQUENCE: 46
gtcggtaagt tcttcaagga agatggca                                             28

SEQ ID NO: 47          moltype = DNA   length = 28
FEATURE                Location/Qualifiers
misc_feature           1..28
                       note = Synthetic Nucleic Acid
source                 1..28
                       mol_type = other DNA
                       organism = synthetic construct
SEQUENCE: 47
tcggtaagtt ctatcaagga agatggca                                             28

SEQ ID NO: 48          moltype = DNA   length = 27
FEATURE                Location/Qualifiers
misc_feature           1..27
                       note = Synthetic Nucleic Acid
source                 1..27
                       mol_type = other DNA
                       organism = synthetic construct
SEQUENCE: 48
cagtcggtaa gttcacatca aggaaga                                              27

SEQ ID NO: 49          moltype = DNA   length = 27
FEATURE                Location/Qualifiers
misc_feature           1..27
                       note = Synthetic Nucleic Acid
source                 1..27
                       mol_type = other DNA
                       organism = synthetic construct
SEQUENCE: 49
cggtaagttc tcaacatcaa ggaagat                                              27

SEQ ID NO: 50          moltype = DNA   length = 26
FEATURE                Location/Qualifiers
misc_feature           1..26
                       note = Synthetic Nucleic Acid
source                 1..26
                       mol_type = other DNA
                       organism = synthetic construct
SEQUENCE: 50
gtcggtaagt tctcatcaag gaagat                                               26
```

```
SEQ ID NO: 51             moltype = DNA   length = 27
FEATURE                   Location/Qualifiers
misc_feature              1..27
                          note = Synthetic Nucleic Acid
source                    1..27
                          mol_type = other DNA
                          organism = synthetic construct
SEQUENCE: 51
ccagtcggta agaacatcaa ggaagat                                          27

SEQ ID NO: 52             moltype = DNA   length = 28
FEATURE                   Location/Qualifiers
misc_feature              1..28
                          note = Synthetic Nucleic Acid
source                    1..28
                          mol_type = other DNA
                          organism = synthetic construct
SEQUENCE: 52
aagccagtcg gtaaacatca aggaagat                                         28

SEQ ID NO: 53             moltype = DNA   length = 27
FEATURE                   Location/Qualifiers
misc_feature              1..27
                          note = Synthetic Nucleic Acid
source                    1..27
                          mol_type = other DNA
                          organism = synthetic construct
SEQUENCE: 53
tcggtaagtt ctgcatcaag gaagatg                                          27

SEQ ID NO: 54             moltype = DNA   length = 27
FEATURE                   Location/Qualifiers
misc_feature              1..27
                          note = Synthetic Nucleic Acid
source                    1..27
                          mol_type = other DNA
                          organism = synthetic construct
SEQUENCE: 54
tcggtaagtt ctaaggaaga tggcatt                                          27

SEQ ID NO: 55             moltype = DNA   length = 29
FEATURE                   Location/Qualifiers
misc_feature              1..29
                          note = Synthetic Nucleic Acid
source                    1..29
                          mol_type = other DNA
                          organism = synthetic construct
SEQUENCE: 55
tcggtaagtt cttcaaggaa gatggcatt                                        29

SEQ ID NO: 56             moltype = DNA   length = 28
FEATURE                   Location/Qualifiers
misc_feature              1..28
                          note = Synthetic Nucleic Acid
source                    1..28
                          mol_type = other DNA
                          organism = synthetic construct
SEQUENCE: 56
agaaagccag tccatcaagg aagatggc                                         28

SEQ ID NO: 57             moltype = DNA   length = 28
FEATURE                   Location/Qualifiers
misc_feature              1..28
                          note = Synthetic Nucleic Acid
source                    1..28
                          mol_type = other DNA
                          organism = synthetic construct
SEQUENCE: 57
agtcggtaag ttcaacatca aggaagat                                         28

SEQ ID NO: 58             moltype = DNA   length = 29
FEATURE                   Location/Qualifiers
misc_feature              1..29
                          note = Synthetic Nucleic Acid
source                    1..29
                          mol_type = other DNA
                          organism = synthetic construct
```

```
SEQUENCE: 58
ccagtcggta agttaacatc aaggaagat                                29

SEQ ID NO: 59           moltype = DNA   length = 29
FEATURE                 Location/Qualifiers
misc_feature            1..29
                        note = Synthetic Nucleic Acid
source                  1..29
                        mol_type = other DNA
                        organism = synthetic construct
SEQUENCE: 59
agtcggtaag ttctaacatc aaggaagat                                29

SEQ ID NO: 60           moltype = DNA   length = 28
FEATURE                 Location/Qualifiers
misc_feature            1..28
                        note = Synthetic Nucleic Acid
source                  1..28
                        mol_type = other DNA
                        organism = synthetic construct
SEQUENCE: 60
ccagtcggta agtaacatca aggaagat                                 28

SEQ ID NO: 61           moltype = DNA   length = 28
FEATURE                 Location/Qualifiers
misc_feature            1..28
                        note = Synthetic Nucleic Acid
source                  1..28
                        mol_type = other DNA
                        organism = synthetic construct
SEQUENCE: 61
tcggtaagtt ctcatcaagg aagatggc                                 28

SEQ ID NO: 62           moltype = DNA   length = 28
FEATURE                 Location/Qualifiers
misc_feature            1..28
                        note = Synthetic Nucleic Acid
source                  1..28
                        mol_type = other DNA
                        organism = synthetic construct
SEQUENCE: 62
agccagtcgg taaaacatca aggaagat                                 28

SEQ ID NO: 63           moltype = DNA   length = 30
FEATURE                 Location/Qualifiers
misc_feature            1..30
                        note = Synthetic Nucleic Acid
source                  1..30
                        mol_type = other DNA
                        organism = synthetic construct
SEQUENCE: 63
tcggtaagtt ctgtcctctg agtaggagct                               30

SEQ ID NO: 64           moltype = DNA   length = 27
FEATURE                 Location/Qualifiers
misc_feature            1..27
                        note = Synthetic Nucleic Acid
source                  1..27
                        mol_type = other DNA
                        organism = synthetic construct
SEQUENCE: 64
taacagtctg agtcggtaag ttctgtc                                  27

SEQ ID NO: 65           moltype = DNA   length = 27
FEATURE                 Location/Qualifiers
misc_feature            1..27
                        note = Synthetic Nucleic Acid
source                  1..27
                        mol_type = other DNA
                        organism = synthetic construct
SEQUENCE: 65
cggtaagttc tgtcagtaac agtctga                                  27
```

```
SEQ ID NO: 66            moltype = DNA  length = 27
FEATURE                  Location/Qualifiers
misc_feature             1..27
                         note = Synthetic Nucleic Acid
source                   1..27
                         mol_type = other DNA
                         organism = synthetic construct
SEQUENCE: 66
cggtaagttc tgtcacagtc tgagtag                                        27

SEQ ID NO: 67            moltype = DNA  length = 27
FEATURE                  Location/Qualifiers
misc_feature             1..27
                         note = Synthetic Nucleic Acid
source                   1..27
                         mol_type = other DNA
                         organism = synthetic construct
SEQUENCE: 67
cggtaagttc tgtccaacag tctgagt                                        27

SEQ ID NO: 68            moltype = DNA  length = 26
FEATURE                  Location/Qualifiers
misc_feature             1..26
                         note = Synthetic Nucleic Acid
source                   1..26
                         mol_type = other DNA
                         organism = synthetic construct
SEQUENCE: 68
tcggtaagtt ctgtccagtc tgagta                                         26

SEQ ID NO: 69            moltype = DNA  length = 26
FEATURE                  Location/Qualifiers
misc_feature             1..26
                         note = Synthetic Nucleic Acid
source                   1..26
                         mol_type = other DNA
                         organism = synthetic construct
SEQUENCE: 69
tcggtaagtt ctgtacagtc tgagta                                         26

SEQ ID NO: 70            moltype = DNA  length = 26
FEATURE                  Location/Qualifiers
misc_feature             1..26
                         note = Synthetic Nucleic Acid
source                   1..26
                         mol_type = other DNA
                         organism = synthetic construct
SEQUENCE: 70
tcggtaagtt ctgtcacagt ctgagt                                         26

SEQ ID NO: 71            moltype = DNA  length = 27
FEATURE                  Location/Qualifiers
misc_feature             1..27
                         note = Synthetic Nucleic Acid
source                   1..27
                         mol_type = other DNA
                         organism = synthetic construct
SEQUENCE: 71
tcggtaagtt ctgtaacagt ctgagta                                        27

SEQ ID NO: 72            moltype = DNA  length = 27
FEATURE                  Location/Qualifiers
misc_feature             1..27
                         note = Synthetic Nucleic Acid
source                   1..27
                         mol_type = other DNA
                         organism = synthetic construct
SEQUENCE: 72
tcggtaagtt ctgtcaacag tctgagt                                        27

SEQ ID NO: 73            moltype = DNA  length = 27
FEATURE                  Location/Qualifiers
misc_feature             1..27
                         note = Synthetic Nucleic Acid
source                   1..27
                         mol_type = other DNA
                         organism = synthetic construct
```

```
SEQUENCE: 73
tcggtaagtt ctgttaacag tctgagt                                              27

SEQ ID NO: 74           moltype = DNA   length = 26
FEATURE                 Location/Qualifiers
misc_feature            1..26
                        note = Synthetic Nucleic Acid
source                  1..26
                        mol_type = other DNA
                        organism = synthetic construct
SEQUENCE: 74
tcggtaagtt ctgtctctga gtagga                                               26

SEQ ID NO: 75           moltype = DNA   length = 25
FEATURE                 Location/Qualifiers
misc_feature            1..25
                        note = Synthetic Nucleic Acid
source                  1..25
                        mol_type = other DNA
                        organism = synthetic construct
SEQUENCE: 75
tcggtaagtt ctgtcctgag tagga                                                25

SEQ ID NO: 76           moltype = DNA   length = 26
FEATURE                 Location/Qualifiers
misc_feature            1..26
                        note = Synthetic Nucleic Acid
source                  1..26
                        mol_type = other DNA
                        organism = synthetic construct
SEQUENCE: 76
tcggtaagtt ctgtctgagt aggagc                                               26

SEQ ID NO: 77           moltype = DNA   length = 25
FEATURE                 Location/Qualifiers
misc_feature            1..25
                        note = Synthetic Nucleic Acid
source                  1..25
                        mol_type = other DNA
                        organism = synthetic construct
SEQUENCE: 77
cggtaagttc tgtccagtct gagta                                                25

SEQ ID NO: 78           moltype = DNA   length = 22
FEATURE                 Location/Qualifiers
misc_feature            1..22
                        note = Synthetic Nucleic Acid
source                  1..22
                        mol_type = other DNA
                        organism = synthetic construct
SEQUENCE: 78
tcggtaagtt ctgtctgagt ag                                                   22

SEQ ID NO: 79           moltype = DNA   length = 25
FEATURE                 Location/Qualifiers
misc_feature            1..25
                        note = Synthetic Nucleic Acid
source                  1..25
                        mol_type = other DNA
                        organism = synthetic construct
SEQUENCE: 79
tcggtaagtt ctgtcgtagg agcta                                                25

SEQ ID NO: 80           moltype = DNA   length = 25
FEATURE                 Location/Qualifiers
misc_feature            1..25
                        note = Synthetic Nucleic Acid
source                  1..25
                        mol_type = other DNA
                        organism = synthetic construct
SEQUENCE: 80
tcggtaagtt ctgtgagtag gagct                                                25
```

```
SEQ ID NO: 81            moltype = DNA  length = 25
FEATURE                  Location/Qualifiers
misc_feature             1..25
                         note = Synthetic Nucleic Acid
source                   1..25
                         mol_type = other DNA
                         organism = synthetic construct
SEQUENCE: 81
cggtaagttc tgtccctgag tagga                                         25

SEQ ID NO: 82            moltype = DNA  length = 27
FEATURE                  Location/Qualifiers
misc_feature             1..27
                         note = Synthetic Nucleic Acid
source                   1..27
                         mol_type = other DNA
                         organism = synthetic construct
SEQUENCE: 82
taagttctgt ccgtctgagt aggagct                                       27

SEQ ID NO: 83            moltype = DNA  length = 28
FEATURE                  Location/Qualifiers
misc_feature             1..28
                         note = Synthetic Nucleic Acid
source                   1..28
                         mol_type = other DNA
                         organism = synthetic construct
SEQUENCE: 83
cggtaagttc tgtcgtagga gctaaaat                                      28

SEQ ID NO: 84            moltype = DNA  length = 28
FEATURE                  Location/Qualifiers
misc_feature             1..28
                         note = Synthetic Nucleic Acid
source                   1..28
                         mol_type = other DNA
                         organism = synthetic construct
SEQUENCE: 84
tctgtccaag cccgctgagt aggagcta                                      28

SEQ ID NO: 85            moltype = DNA  length = 27
FEATURE                  Location/Qualifiers
misc_feature             1..27
                         note = Synthetic Nucleic Acid
source                   1..27
                         mol_type = other DNA
                         organism = synthetic construct
SEQUENCE: 85
cggtaagttc tgtctaacag tctgagt                                       27

SEQ ID NO: 86            moltype = DNA  length = 28
FEATURE                  Location/Qualifiers
misc_feature             1..28
                         note = Synthetic Nucleic Acid
source                   1..28
                         mol_type = other DNA
                         organism = synthetic construct
SEQUENCE: 86
agttctgtcc aacagtctga gtaggagc                                      28

SEQ ID NO: 87            moltype = DNA  length = 27
FEATURE                  Location/Qualifiers
misc_feature             1..27
                         note = Synthetic Nucleic Acid
source                   1..27
                         mol_type = other DNA
                         organism = synthetic construct
SEQUENCE: 87
taagttctgt ccaatctgag taggagc                                       27

SEQ ID NO: 88            moltype = DNA  length = 26
FEATURE                  Location/Qualifiers
misc_feature             1..26
                         note = Synthetic Nucleic Acid
source                   1..26
                         mol_type = other DNA
                         organism = synthetic construct
```

```
SEQUENCE: 88
cggtaagttc tgtcaacagt ctgagt                                          26

SEQ ID NO: 89           moltype = DNA   length = 26
FEATURE                 Location/Qualifiers
misc_feature            1..26
                        note = Synthetic Nucleic Acid
source                  1..26
                        mol_type = other DNA
                        organism = synthetic construct
SEQUENCE: 89
tcggtaagtt ctgtaacagt ctgagt                                          26

SEQ ID NO: 90           moltype = DNA   length = 30
FEATURE                 Location/Qualifiers
misc_feature            1..30
                        note = Synthetic Nucleic Acid
source                  1..30
                        mol_type = other DNA
                        organism = synthetic construct
SEQUENCE: 90
cggtaagttc tgtcctcaag gaagatggca                                      30

SEQ ID NO: 91           moltype = DNA   length = 28
FEATURE                 Location/Qualifiers
misc_feature            1..28
                        note = Synthetic Nucleic Acid
source                  1..28
                        mol_type = other DNA
                        organism = synthetic construct
SEQUENCE: 91
tcggtaagtt ctgtcgaaga tggcattt                                        28

SEQ ID NO: 92           moltype = DNA   length = 27
FEATURE                 Location/Qualifiers
misc_feature            1..27
                        note = Synthetic Nucleic Acid
source                  1..27
                        mol_type = other DNA
                        organism = synthetic construct
SEQUENCE: 92
cggtaagttc tgtcaagatg gcatttc                                         27

SEQ ID NO: 93           moltype = DNA   length = 28
FEATURE                 Location/Qualifiers
misc_feature            1..28
                        note = Synthetic Nucleic Acid
source                  1..28
                        mol_type = other DNA
                        organism = synthetic construct
SEQUENCE: 93
cggtaagttc tgtccgaaga tggcattt                                        28

SEQ ID NO: 94           moltype = DNA   length = 30
FEATURE                 Location/Qualifiers
misc_feature            1..30
                        note = Synthetic Nucleic Acid
source                  1..30
                        mol_type = other DNA
                        organism = synthetic construct
SEQUENCE: 94
ctccaacatc aaggaagatg gcatttctag                                      30

SEQ ID NO: 95           moltype = DNA   length = 20
FEATURE                 Location/Qualifiers
misc_feature            1..20
                        note = Synthetic Nucleic Acid
source                  1..20
                        mol_type = other DNA
                        organism = synthetic construct
SEQUENCE: 95
ctgagtggaa ggcggtaaac                                                 20
```

```
SEQ ID NO: 96          moltype = DNA  length = 20
FEATURE                Location/Qualifiers
misc_feature           1..20
                       note = Synthetic Nucleic Acid
source                 1..20
                       mol_type = other DNA
                       organism = synthetic construct
SEQUENCE: 96
gaagtttcag ggccaagtca                                                     20

SEQ ID NO: 97          moltype = DNA  length = 30
FEATURE                Location/Qualifiers
misc_feature           1..30
                       note = Synthetic Nucleic Acid
source                 1..30
                       mol_type = other DNA
                       organism = synthetic construct
SEQUENCE: 97
ctcatacctt ctgcttcaag gaagatggca                                          30

SEQ ID NO: 98          moltype = DNA  length = 30
FEATURE                Location/Qualifiers
misc_feature           1..30
                       note = Synthetic Nucleic Acid
source                 1..30
                       mol_type = other DNA
                       organism = synthetic construct
SEQUENCE: 98
ctccaacatc aaggaagatg gcatttctag                                          30

SEQ ID NO: 99          moltype = DNA  length = 21
FEATURE                Location/Qualifiers
misc_feature           1..21
                       note = Synthetic Nucleic Acid
source                 1..21
                       mol_type = other DNA
                       organism = synthetic construct
SEQUENCE: 99
aacatcaagg aagatggcat t                                                   21

SEQ ID NO: 100         moltype = DNA  length = 21
FEATURE                Location/Qualifiers
misc_feature           1..21
                       note = Synthetic Nucleic Acid
source                 1..21
                       mol_type = other DNA
                       organism = synthetic construct
SEQUENCE: 100
tccaacatca aggaagatgg c                                                   21

SEQ ID NO: 101         moltype = DNA  length = 21
FEATURE                Location/Qualifiers
misc_feature           1..21
                       note = Synthetic Nucleic Acid
source                 1..21
                       mol_type = other DNA
                       organism = synthetic construct
SEQUENCE: 101
acctccaaca tcaaggaaga t                                                   21

SEQ ID NO: 102         moltype = RNA  length = 21
FEATURE                Location/Qualifiers
misc_feature           1..21
                       note = Synthetic Nucleic Acid
source                 1..21
                       mol_type = other RNA
                       organism = synthetic construct
SEQUENCE: 102
gagtaacagt ctgagtagga g                                                   21

SEQ ID NO: 103         moltype = RNA  length = 21
FEATURE                Location/Qualifiers
misc_feature           1..21
                       note = Synthetic Nucleic Acid
source                 1..21
                       mol_type = other RNA
                       organism = synthetic construct
```

```
SEQUENCE: 103
tgtgtcacca gagtaacagt c                                              21

SEQ ID NO: 104         moltype = RNA   length = 21
FEATURE                Location/Qualifiers
misc_feature           1..21
                       note = Synthetic Nucleic Acid
source                 1..21
                       mol_type = other RNA
                       organism = synthetic construct
SEQUENCE: 104
aaccacaggt tgtgtcacca g                                              21

SEQ ID NO: 105         moltype = RNA   length = 21
FEATURE                Location/Qualifiers
misc_feature           1..21
                       note = Synthetic Nucleic Acid
source                 1..21
                       mol_type = other RNA
                       organism = synthetic construct
SEQUENCE: 105
tttccttagt aaccacaggt t                                              21

SEQ ID NO: 106         moltype = RNA   length = 21
FEATURE                Location/Qualifiers
misc_feature           1..21
                       note = Synthetic Nucleic Acid
source                 1..21
                       mol_type = other RNA
                       organism = synthetic construct
SEQUENCE: 106
gagatggcag tttccttagt a                                              21

SEQ ID NO: 107         moltype = RNA   length = 21
FEATURE                Location/Qualifiers
misc_feature           1..21
                       note = Synthetic Nucleic Acid
source                 1..21
                       mol_type = other RNA
                       organism = synthetic construct
SEQUENCE: 107
ttctagtttg gagatggcag t                                              21

SEQ ID NO: 108         moltype = RNA   length = 21
FEATURE                Location/Qualifiers
misc_feature           1..21
                       note = Synthetic Nucleic Acid
source                 1..21
                       mol_type = other RNA
                       organism = synthetic construct
SEQUENCE: 108
aagatggcat ttctagtttg g                                              21

SEQ ID NO: 109         moltype = RNA   length = 21
FEATURE                Location/Qualifiers
misc_feature           1..21
                       note = Synthetic Nucleic Acid
source                 1..21
                       mol_type = other RNA
                       organism = synthetic construct
SEQUENCE: 109
aacatcaagg aagatggcat t                                              21

SEQ ID NO: 110         moltype = RNA   length = 21
FEATURE                Location/Qualifiers
misc_feature           1..21
                       note = Synthetic Nucleic Acid
source                 1..21
                       mol_type = other RNA
                       organism = synthetic construct
SEQUENCE: 110
aggtacctcc aacatcaagg a                                              21
```

```
SEQ ID NO: 111          moltype = RNA  length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 111
ctgccagagc aggtacctcc a                                              21

SEQ ID NO: 112          moltype = RNA  length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 112
cggttgaaat ctgccagagc a                                              21

SEQ ID NO: 113          moltype = RNA  length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 113
tgtccaagcc cggttgaaat c                                              21

SEQ ID NO: 114          moltype = RNA  length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 114
cggtaagttc tgtccaagcc c                                              21

SEQ ID NO: 115          moltype = RNA  length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 115
gaaagccagt cggtaagttc t                                              21

SEQ ID NO: 116          moltype = RNA  length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 116
atcaagcaga gaaagccagt c                                              21

SEQ ID NO: 117          moltype = RNA  length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 117
ttataacttg atcaagcaga g                                              21

SEQ ID NO: 118          moltype = RNA  length = 21
FEATURE                 Location/Qualifiers
misc_feature            1..21
                        note = Synthetic Nucleic Acid
source                  1..21
                        mol_type = other RNA
                        organism = synthetic construct
```

```
SEQUENCE: 118
ctctgtgatt ttataacttg a                                              21

SEQ ID NO: 119          moltype = RNA   length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 119
caccatcacc ctctgtgatt t                                              21

SEQ ID NO: 120          moltype = RNA   length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 120
caaggtcacc caccatcacc c                                              21

SEQ ID NO: 121          moltype = RNA   length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 121
ttgatatcct caaggtcacc c                                              21

SEQ ID NO: 122          moltype = RNA   length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 122
gatcatctcg ttgatatcct c                                              21

SEQ ID NO: 123          moltype = RNA   length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 123
tctgcttgat gatcatctcg t                                              21

SEQ ID NO: 124          moltype = RNA   length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 124
ggcatttcta gtttggagat g                                              21

SEQ ID NO: 125          moltype = RNA   length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 125
caaggaagat ggcatttcta g                                              21
```

```
SEQ ID NO: 126          moltype = RNA  length = 21
FEATURE                 Location/Qualifiers
misc_feature            1..21
                        note = Synthetic Nucleic Acid
source                  1..21
                        mol_type = other RNA
                        organism = synthetic construct
SEQUENCE: 126
cctccaacat caaggaagat g                                            21

SEQ ID NO: 127          moltype = DNA  length = 233
FEATURE                 Location/Qualifiers
source                  1..233
                        mol_type = genomic DNA
                        organism = Homo sapiens
SEQUENCE: 127
ctcctactca gactgttact ctggtgacac aacctgtggt tactaaggaa actgccatct   60
ccaaactaga aatgccatct tccttgatgt tggaggtacc tgctctggca gatttcaacc  120
gggcttggac agaacttacc gactggcttt ctctgcttga tcaagttata aaatcacaga  180
gggtgatggt gggtgacctt gaggatatca acgagatgat catcaagcag aag         233

SEQ ID NO: 128          moltype = DNA  length = 251
FEATURE                 Location/Qualifiers
source                  1..251
                        mol_type = genomic DNA
                        organism = Homo sapiens
SEQUENCE: 128
aaacccaaaa tattttagct cctactcaga ctgttactct ggtgacacaa cctgtggtta   60
ctaaggaaac tgccatctcc aaactagaaa tgccatcttc cttgatgttg gaggtacctg  120
ctctggcaga tttcaaccgg gcttggacag aacttaccga ctggctttct ctgcttgatc  180
aagttataaa atcacagagg gtgatggtgg gtgaccttga ggatatcaac gagatgatca  240
tcaagcagaa g                                                      251
```